United States Patent [19]
Yoshinari et al.

[11] Patent Number: 5,756,993
[45] Date of Patent: May 26, 1998

[54] MASS SPECTROMETER

[75] Inventors: Kiyomi Yoshinari, Hitachi; Yoichi Ose, Mito; Katsuhiro Nakagawa, Hitachioota; Yoshiaki Kato, Mito, all of Japan

[73] Assignee: Hitachi, Ltd., Tokyo, Japan

[21] Appl. No.: 754,356

[22] Filed: Nov. 22, 1996

[30] Foreign Application Priority Data

Dec. 1, 1995  [JP]  Japan .................. 7-313826

[51] Int. Cl.[6] ............................ H01J 49/26
[52] U.S. Cl. ........................ 250/281; 250/283
[58] Field of Search ............... 250/281, 282, 250/283, 292

[56] References Cited

U.S. PATENT DOCUMENTS

| | | | |
|---|---|---|---|
| 3,922,544 | 11/1975 | Maul et al. | 250/296 |
| 4,047,030 | 9/1977 | Lobach | 250/281 |
| 4,481,415 | 11/1984 | Takeda et al. | 250/292 |
| 5,464,975 | 11/1995 | Kirchner et al. | 250/281 |
| 5,464,985 | 11/1995 | Cornish et al. | 250/396 R |
| 5,481,107 | 1/1996 | Takada et al. | 250/281 |
| 5,572,022 | 11/1996 | Schwartz et al. | 250/292 |

*Primary Examiner*—Kiet T. Nguyen
*Attorney, Agent, or Firm*—Kenyon & Kenyon

[57] ABSTRACT

A sample separated through a pre-processor part having a gas chromatography (GC) or a liquid chromatography (LC) and a moving bed eliminating part is ionized by an ion source and mass-analyzed by a mass-analyzing part. The mass-analyzed ions are deflected and focused by a deflecting portion and a focusing portion in a deflecting and focusing part, and is detected by an ion detecting part. The result of detection is processed by a data processing part.

24 Claims, 20 Drawing Sheets

Ey DISTRIBUTION

Ey DISTRIBUTION

ION BEAM FROM MASS ANALYZING PART

ION TRAJECTORY ($\Delta E: 5 \sim 2000 eV$)

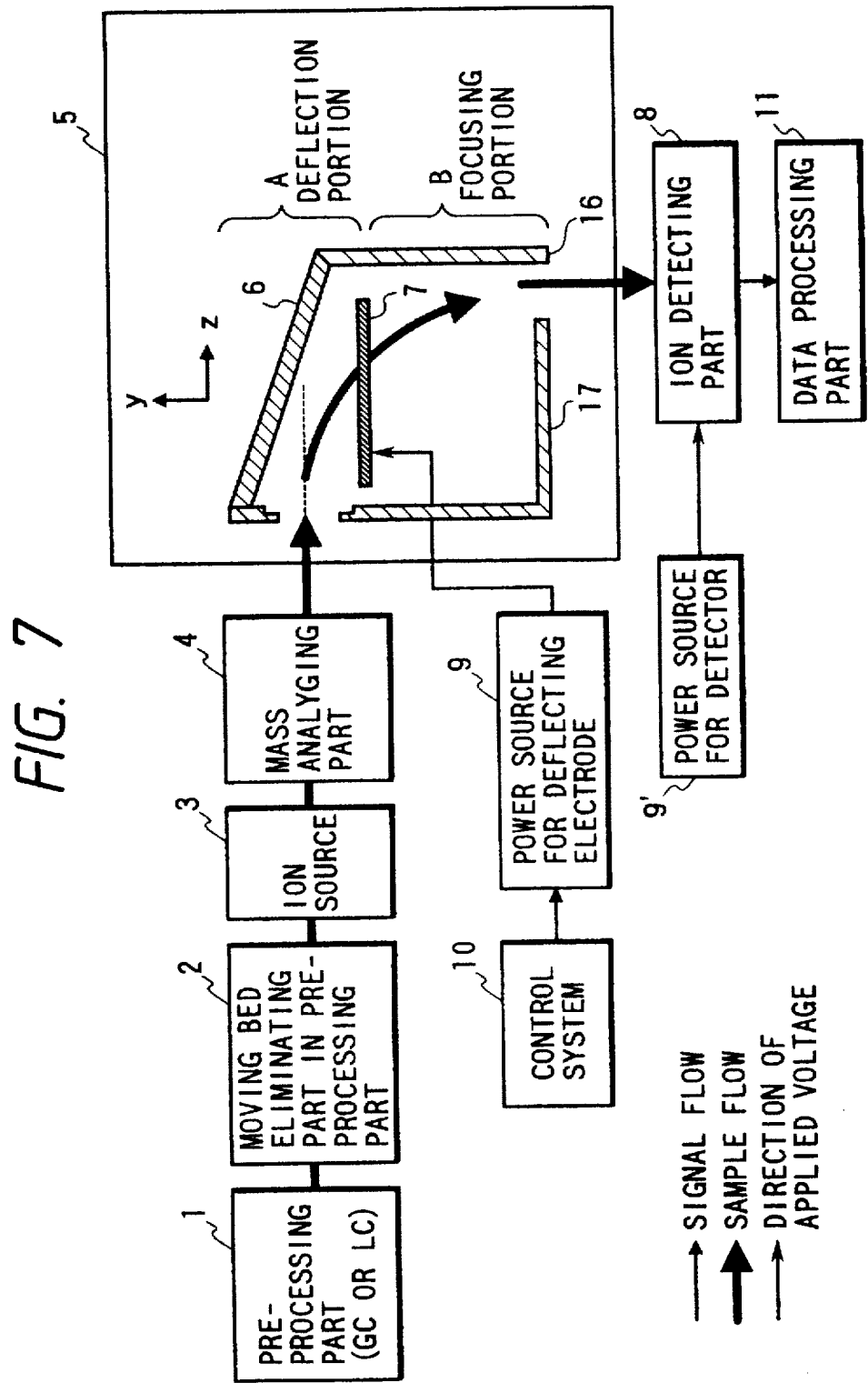

ION BEAM FROM MASS ANALYZING PART

ION TRAJECTORY ($\Delta E: 5\sim2000$ eV)

FIG. 9A ION BEAM FROM MASS ANALYZING PART →
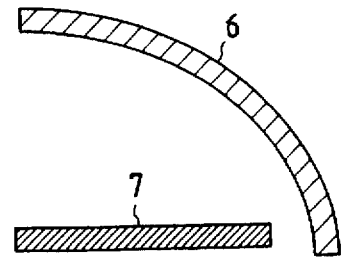
FIG. 9B ION BEAM FROM MASS ANALYZING PART →
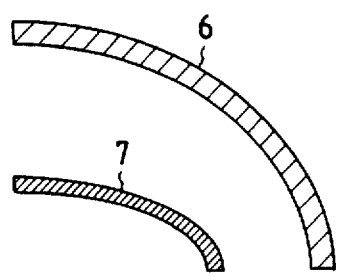
FIG. 10A ION BEAM FROM MASS ANALYZING PART →
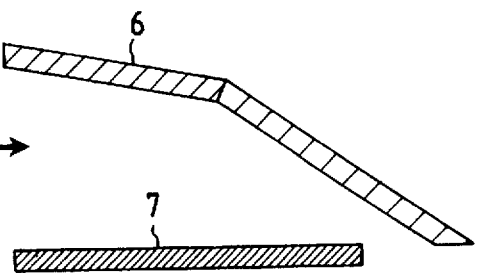
FIG. 10B ION BEAM FROM MASS ANALYZING PART →
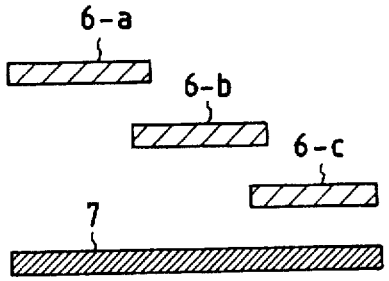

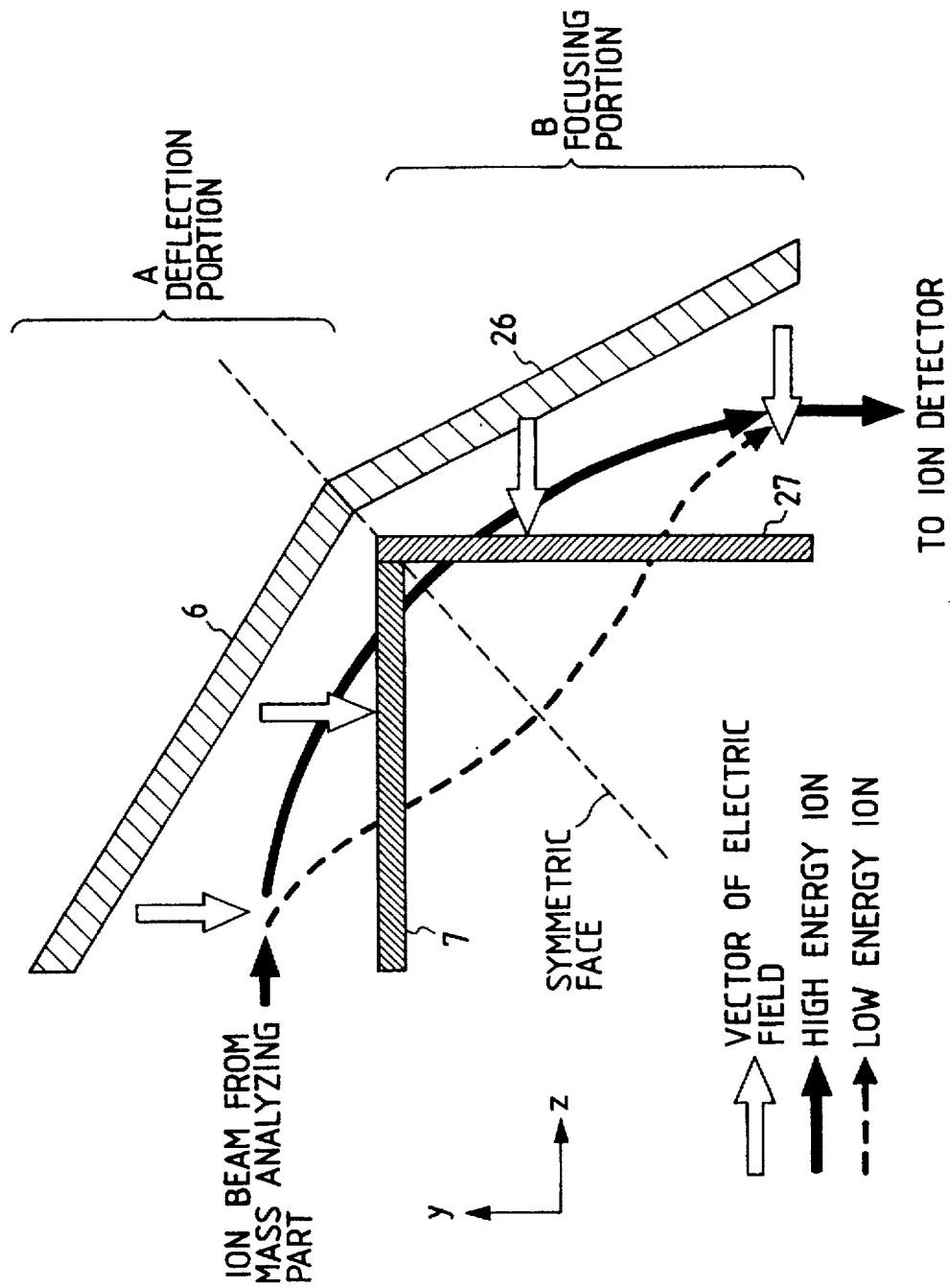

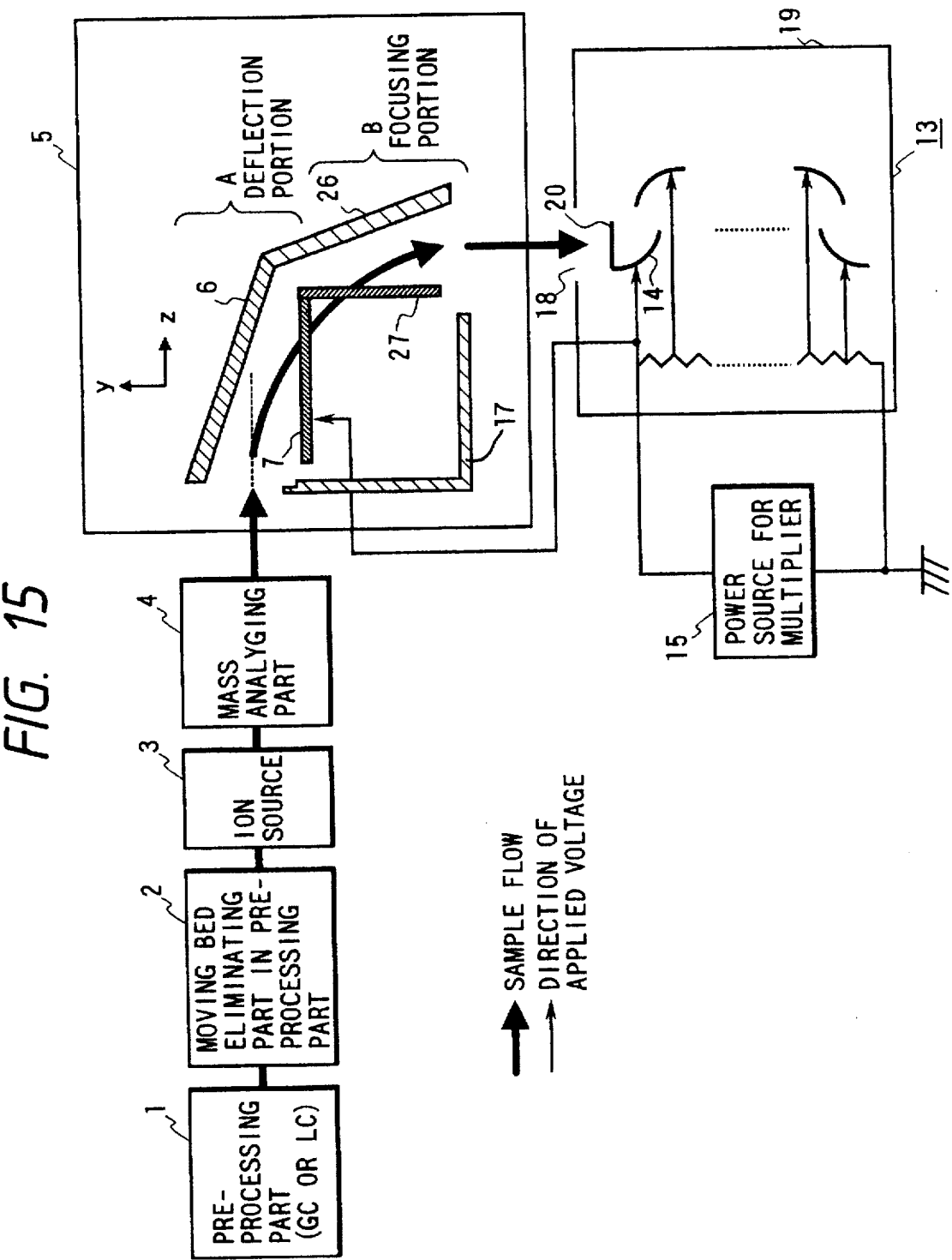

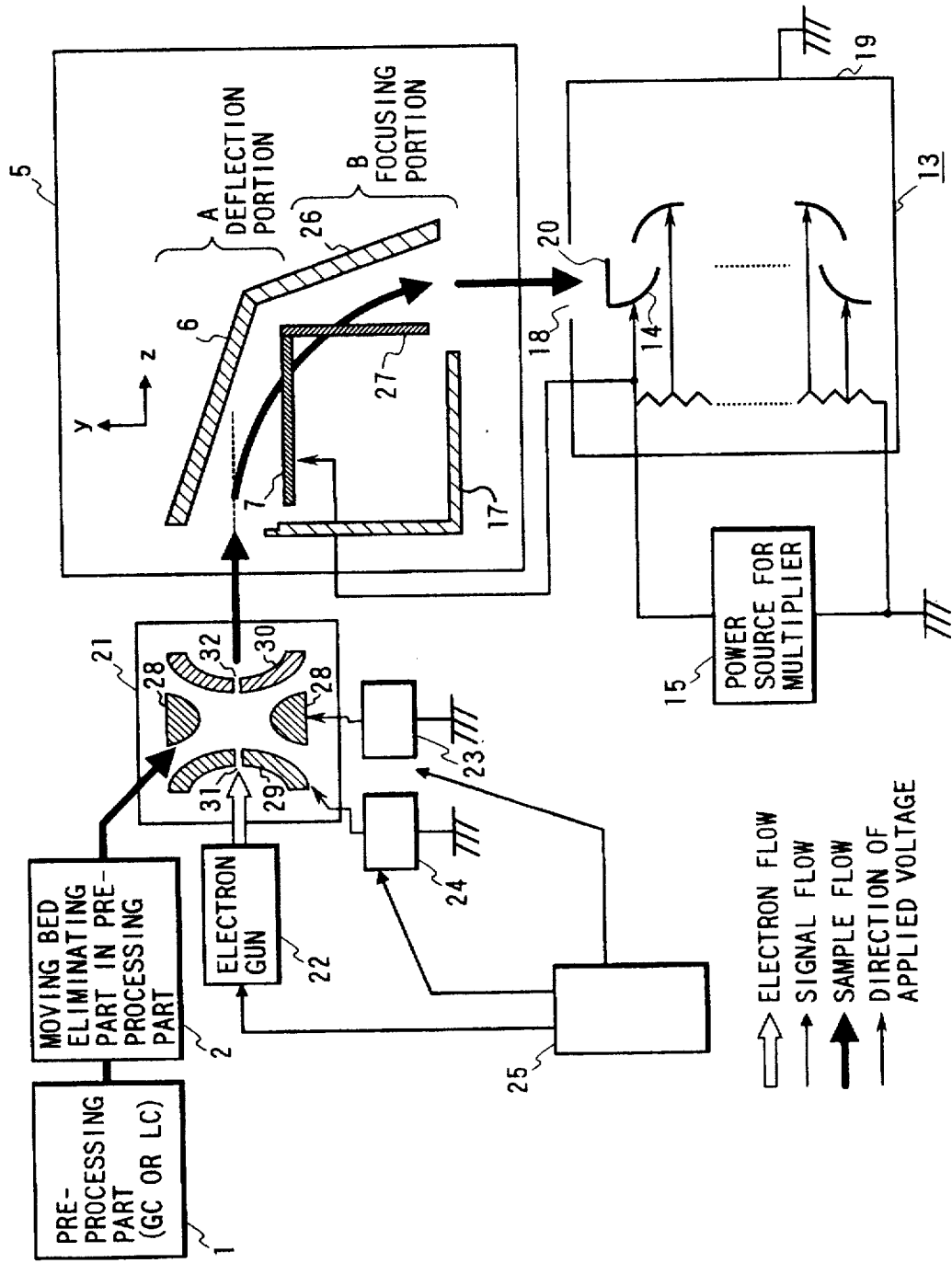

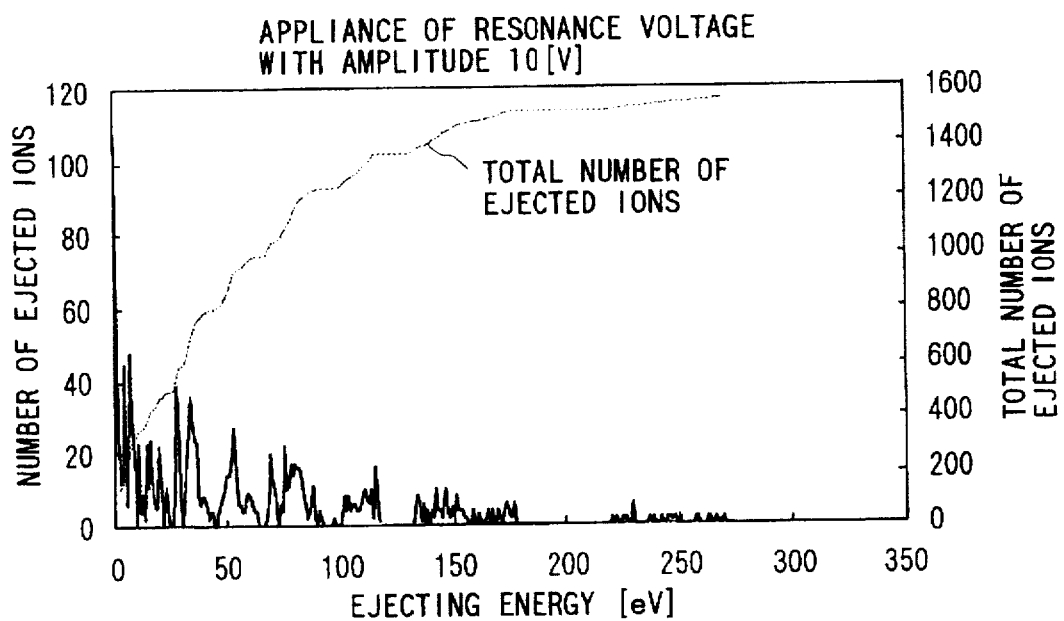
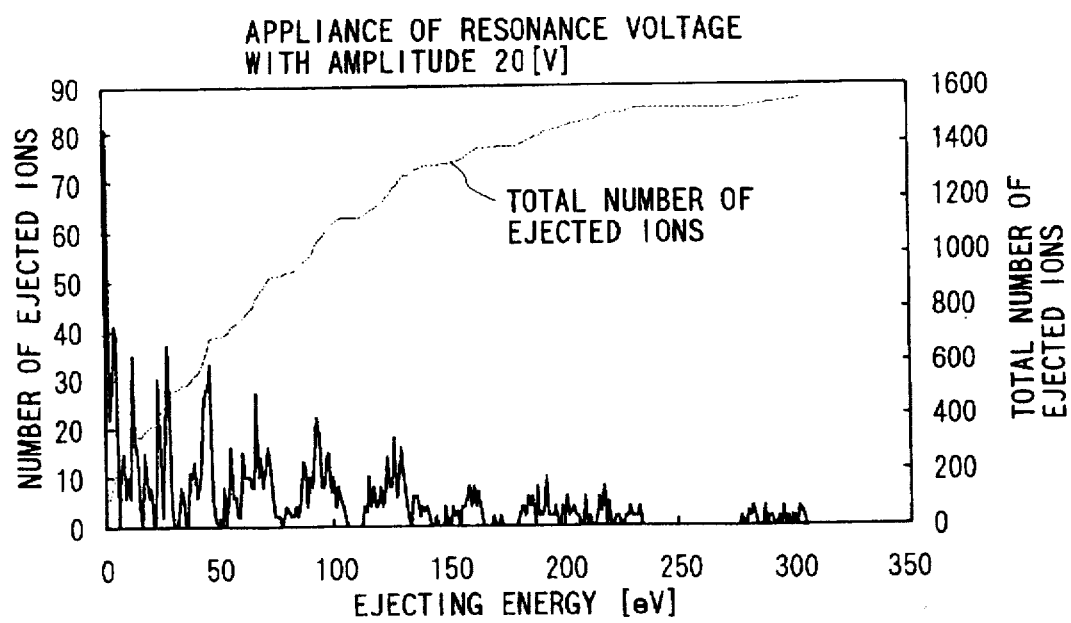

MASS SPECTROMETER

BACKGROUND OF THE INVENTION

The present invention relates to a mass spectrometer, in particular to a mass spectrometer for detecting a mass-analyzed ion, avoiding the occurrence of noises due to a neutral molecular gas.

When a mixture sample is mass-analyzed, it becomes possible to mass-analyze with higher accuracy by using a mass spectrometer in which a pre-processing part and a mass-analyzing part are separated to each other. Where, in the pre-processing part, the mixture sample is separated into its components, and in the mass-analyzing part, the mass-to-charge ratio of the separated sample is analyzed. Usually, a gas chromatography or a liquid chromatography is used as the pre-processing part. A new apparatus has recently been developed and begun to use, in which such a pre-processing part and the mass-analyzing part are combined.

In the pre-processing part using the gas chromatography or the liquid chromatography, a mixture sample is flowed to a column packed a fixed bed, along with a moving bed, that is, a neutral molecular gas (in the gas chromatography) or a solvent (in the liquid chromatography). As a result, the mixture sample can be isolated from the fixed bed due to the difference of affinity. Because the isolated sample still includes the moving bed, it is necessary to eliminate the moving bet to mass-analyze the sample. Usually, in the pre-processing part using the liquid chromatography, the solvent is evaporated and then eliminated. Accordingly, in the pre-processing part using either of the gas chromatography and the liquid chromatography, the moving bed becomes the neutral gas after the isolation of the sample.

Usually, an eliminating unit for the neutral gas is provided between the pre-processing part and the mass-analyzing part. However, the neutral gas can not eliminated completely even through the neutral gas eliminating unit and passes into the mass-analyzing part. Accordingly, the neutral gas is flowed out of the mass-analyzing part along with the mass-analyzed ion. It is well-known that if a detector is provided in a direction of the axis along the direction of ejection of an ion beam from the mass-analyzing part, a noise occurs due to the neutral gas when the mass-analyzed ion is detected. Particularly, in the pre-processing part using the liquid chromatography, the problem of the occurrence of noises is very serious, which occurs due to the neutral molecules of the solvent of the liquid chromatography, because the amount of the neutral gas produced by the evaporation of the solvent is very large as compared with the case of the gas chromatography, the detector is contaminated by the change of the neutral gas into liquid, and so on.

As the conventional and basic method of deflecting an ion beam, there are some methods, namely, a method of deflecting the ion beam through the constant electric field generated between parallel plates applied the potential difference as shown in FIG. 21, or a method of deflecting the ion beam through an electric field generated between an electrode bent along a direction of deflection and a plane electrode as shown in FIG. 22.

A distribution of potentials and a result of calculation concerning trajectories of ions having energy aberration within the range from 5 to 2000 eV are shown in FIGS. 23B and 23A, respectively, in which the conventional deflecting electrodes are arranged as shown in FIG. 22. In this example, the ions to be mass-analyzed are positive, the same negative voltage, 1.4 kV, is applied to a deflecting electrode D and a housing of an ion detector, and another electrode is at the ground potential.

As clearly seen from these figures, if the ion beam from the mass-analyzing part has the energy aberration, the ion beam expands in the deflecting field produced by the conventional deflecting electrodes, and thus the efficiency of detection is deteriorated. this may be caused mainly by the following two facts. (1) The component in a direction of deflection of the electric field generated by the electrodes is decreased as the ion travels along a direction of ejection of the ion beam from the mass-analyzing part. Accordingly, because the deflecting force is decreased as the kinetic energy or velocity of the ions in the direction of ejection thereof is increased, the angle of deflection of the ion is decreased and the ion beam expands as the kinetic energy is increased. Where, the angle of deflection means an angle made by the ion beam after deflection with the direction of ejection of the ion beam from the mass-analyzing part. (2) The component in a direction of ejection of the ion beam from the mass-analyzing part, of the electric field generated by the electrodes increases, as the ion travels along a direction of ejection of the ion beam from the mass-analyzing part. Accordingly, the ion with higher energy or higher velocity ion in a direction of ejection is more accelerated in a direction of acceleration of the ion. Accordingly, the angle of deflection of the ion with higher energy becomes smaller and the width of the ion beam becomes wider.

SUMMARY OF THE INVENTION

An object of the present invention is to provide a mass spectrometer which can avoid noises due to neutral molecules by deflecting and detecting the mass-analyzed ion.

Another object of the present invention is to provide a mass spectrometer which can avoid noises due to neutral molecules by deflecting and detecting the mass-analyzed ion, and which can suppress the expansion of an ion beam caused by energy aberration of the mass-analyzed ions, wherein it is possible to detect the ion with a higher efficiency and with a higher sensitivity.

In a mass spectrometer according to the present invention, ions are mass-analyzed by a mass analyzer, the mass-analyzed ions are deflected by an ion deflecting device, the deflected ions are focused by a focusing device, and the focused ions are detected by an ion detector.

While the mass-analyzed ions are detected after deflecting by the ion deflecting device, the neutral molecule can not deflected by the ion deflecting device, by reason of its characteristic of neutrality. As a result, the occurrence of noises due to the neutral molecules can be avoided.

When the mass-analyzed ions have the energy aberration, the ions are dispersed by the ion deflecting device in accordance with the magnitude of its energy. However, the expansion of the ion beam can be suppressed by the ion focusing device, because the dispersed ion beam is focused by the ion focusing device. As a result, the mass-analyzed ions can be detected with a higher efficiency and with a higher sensitivity.

In a preferred embodiment of the present invention, a stronger power of deflection is provided as the energy of an ion becomes higher. Accordingly, the expansion of the ion beam due to its dispersion caused while the ions travel in the deflecting device can be more suppressed, because the degree of dispersion of the dispersed ions are suppressed by the force of deflection, in addition to that the dispersed ions are focused by the ion focusing device.

Other objects and advantages of this invention will clearly appear from the description and from the accompanying drawing.

BRIEF DESCRIPTION OF THE DRAWINGS

FIG. 7 is a schematic view showing the whole mass spectrometer according to a second embodiment of the present invention.

FIG. 9A is a sectional view of deflecting electrodes of a mass spectrometer according to a third embodiment of the present invention.

FIG. 9B is a sectional view of a modified example of the deflecting electrodes of the mass spectrometer according to the third embodiment of the present invention.

FIG. 10A is a sectional view of deflecting electrodes of a mass spectrometer according to a fourth embodiment of the present invention.

FIG. 10B is a sectional view of a modified example of the deflecting electrodes of the mass spectrometer according to the fourth embodiment of the present invention.

FIG. 11 is a sectional view showing the deflecting and focusing part of the mass spectrometer according to the fifth embodiment of the present invention.

FIG. 15 is a schematic view showing the whole mass spectrometer according to a seventh embodiment of the present invention.

FIG. 18 is a schematic view showing the whole mass spectrometer according to a eighth embodiment of the present invention.

FIG. 20B is a view showing a distribution of energy of singly charged ions with 100 (amu), where a resonance-ejection point is q=0.897 at the time of the ejection from the ion trap, and the amplitude of an applied resonance voltage equals to 10V.

FIG. 20C is a view showing a distribution of energy of singly charged ions with 100 (amu), where a resonance-ejection point is q=0.897 at the time of the ejection from the ion trap, and the amplitude of an applied resonance voltage equals to 20V.

DESCRIPTION OF THE PREFERRED EMBODIMENTS

Embodiment 1

Figure 1:
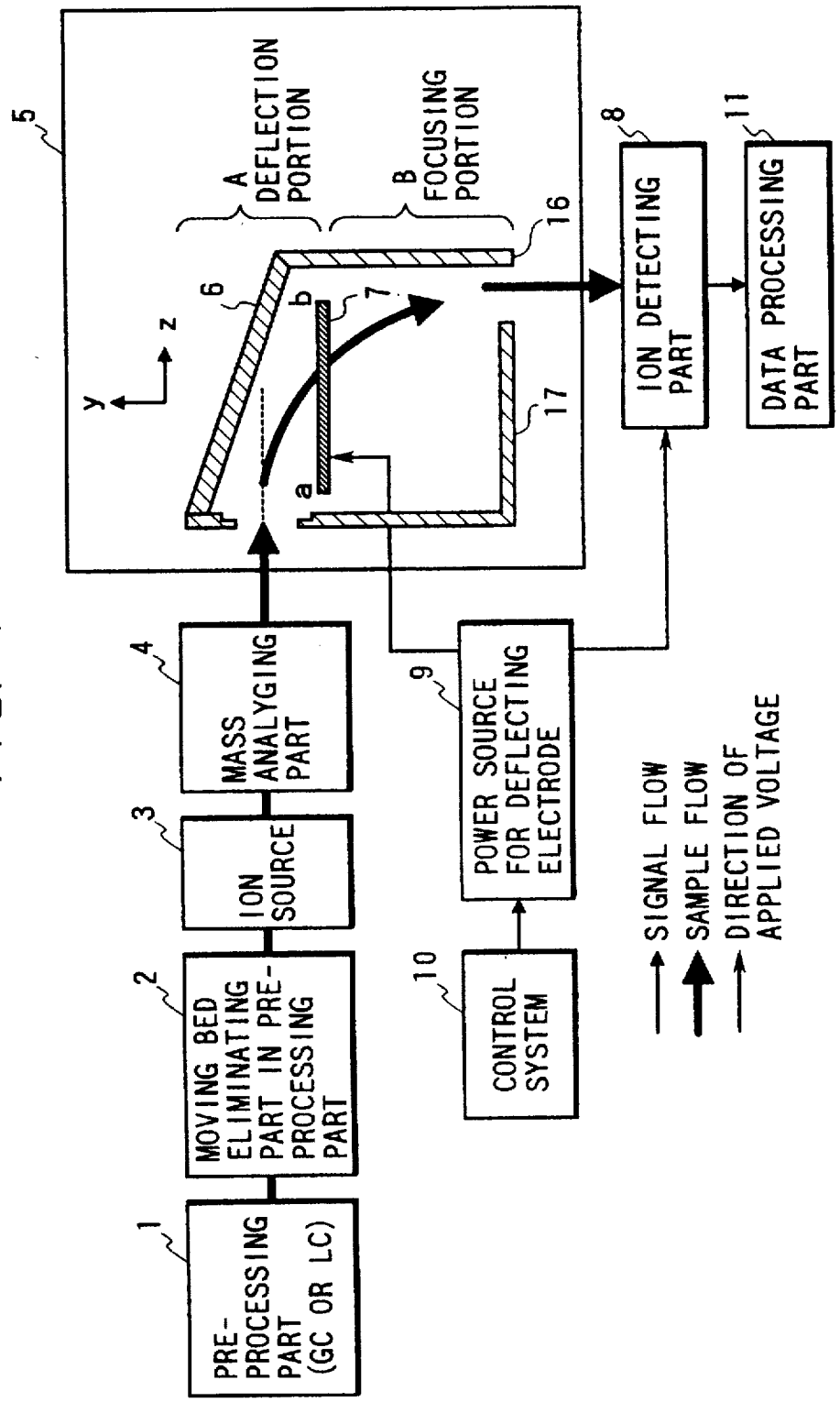
FIG. 1 is a schematic view showing the whole mass spectrometer according to a first embodiment of the present invention.

Firstly, a first embodiment will be explained with reference to FIG. 1 through FIG. 6. FIG. 1 is a schematic view showing the whole mass spectrometer according to the first embodiment of the present invention. A mixture sample to be mass-analyzed is separated into its components through a pre-processor part 1 which comprises a gas chromatography (GC) or a liquid chromatography (LC). Then, a moving bed of the sample from the pre-processing part is eliminated by using a moving bed eliminating part. The sample is ionized by an ion source 3 and mass-analyzed by a mass-analyzing part 4. The mass-analyzed ion is deflected and focused by a deflecting portion A and a focusing portion B, respectively, in a deflecting and focusing part 5, and is detected by an ion detecting part 8. The result of detection is processed by a data processing part 11. The deflecting and focusing part 5 comprises the deflecting portion A for deflecting the ion beam and the focusing portion B for focusing the deflected ion beam.

The deflecting portion A will be explained next. In order that the ion can receive a force in a direction (−y direction) to be deflected, a potential difference is applied between electrodes 6 and 7 and thereby a deflecting field is generated in a space formed between the electrodes 6 and 7 which is arranged to sandwich the ion beam injected into the deflecting and focusing part 5 in the y direction. The electrode 7 is referred hereinafter to as an inside deflecting electrode, positioned at a side to which the ion is deflected, and the electrode 6 opposite to the electrode 7 is referred to as an outside deflecting electrode.

Figure 2:
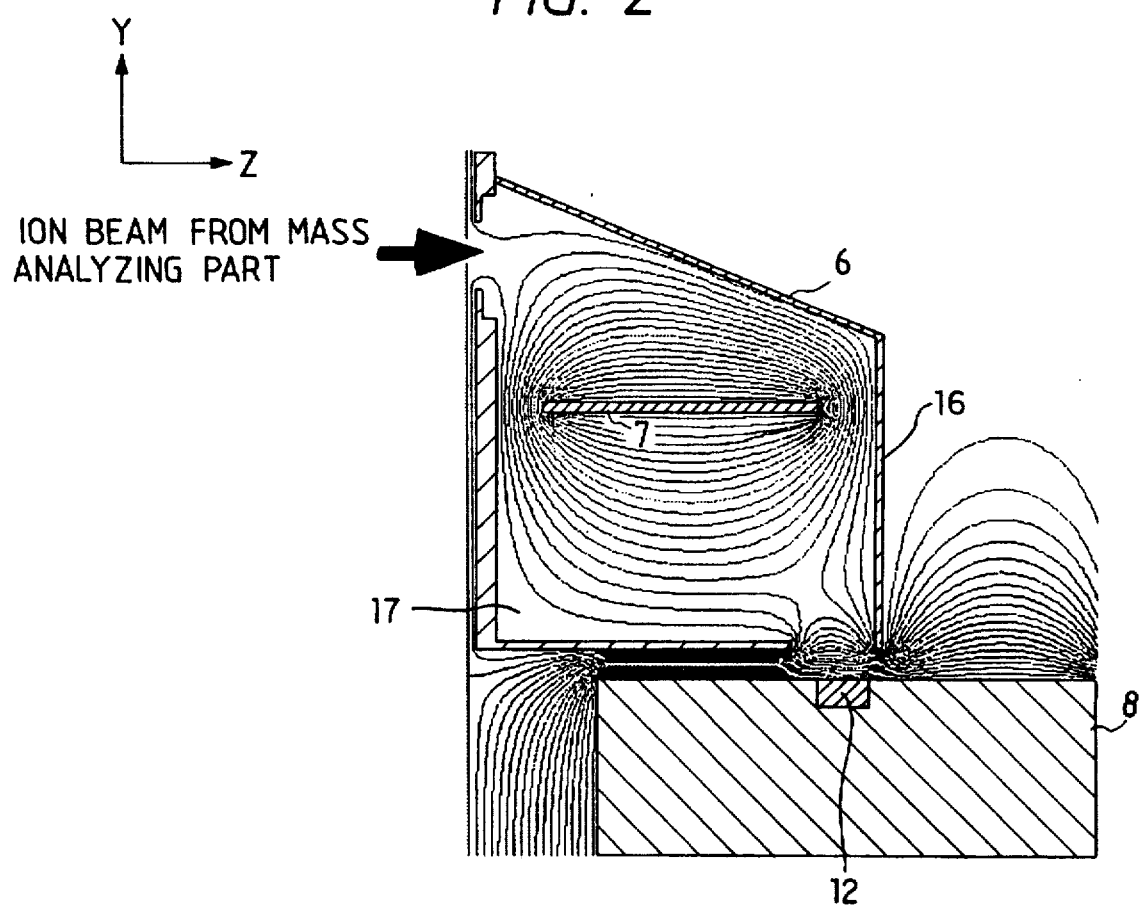
FIG. 2 is a sectional view of a part of a ion detecting part and a deflecting and focusing part in the first embodiment of the present invention.
Figure 3A:
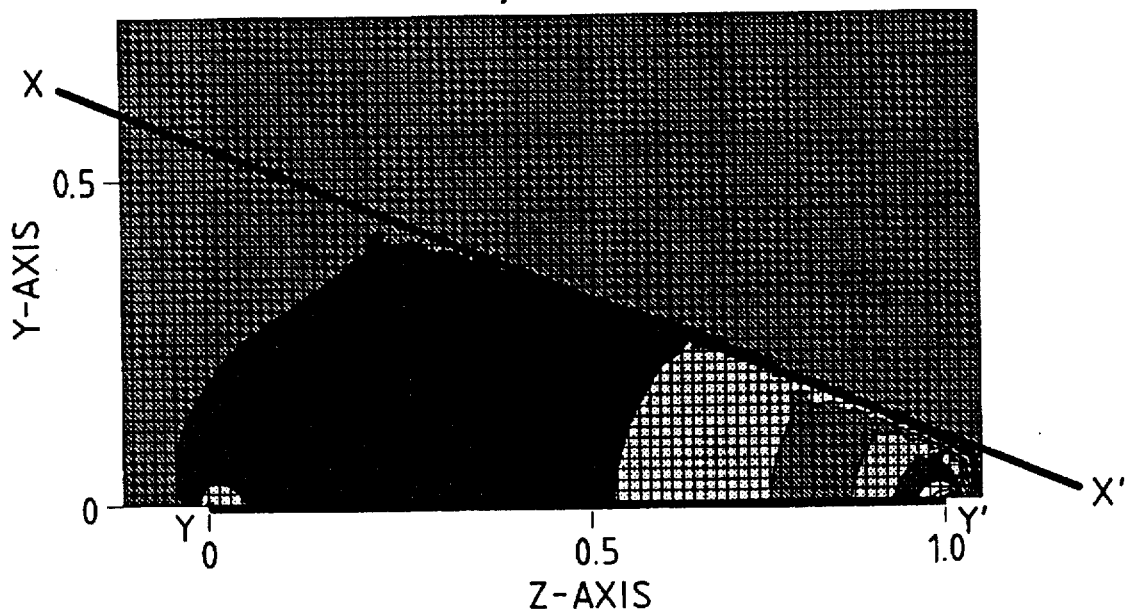
FIG. 3A is a view showing a two dimensional distribution of an electric field (component in a direction of deflection) at a deflecting portion of the deflecting and focusing part in the first embodiment of the present invention.
Figure 3B:
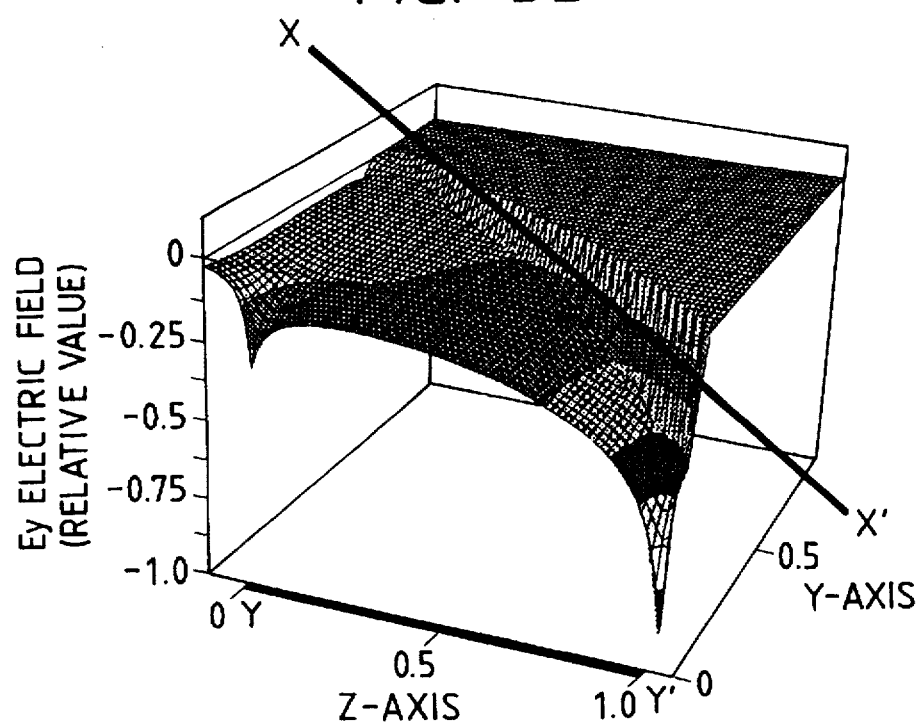
FIG. 3B is a view showing a three dimensional distribution of an electric field (component in a direction of deflection) at a deflecting portion of the deflecting and focusing part in the first embodiment of the present invention.
Figure 4A:
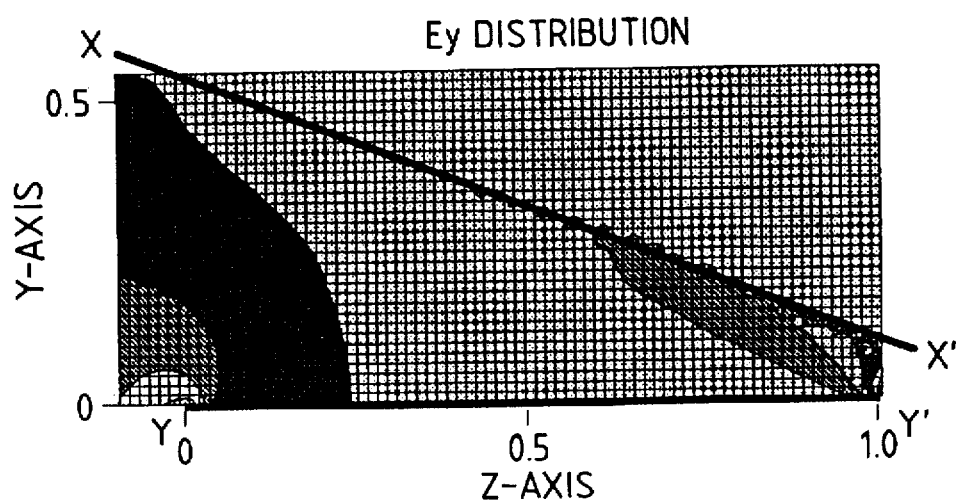
FIG. 4A is a view showing a two dimensional distribution of an electric field (component in a direction of injection of an ion beam) at a deflecting portion of the deflecting and focusing part in the first embodiment of the present invention.
Figure 4B:
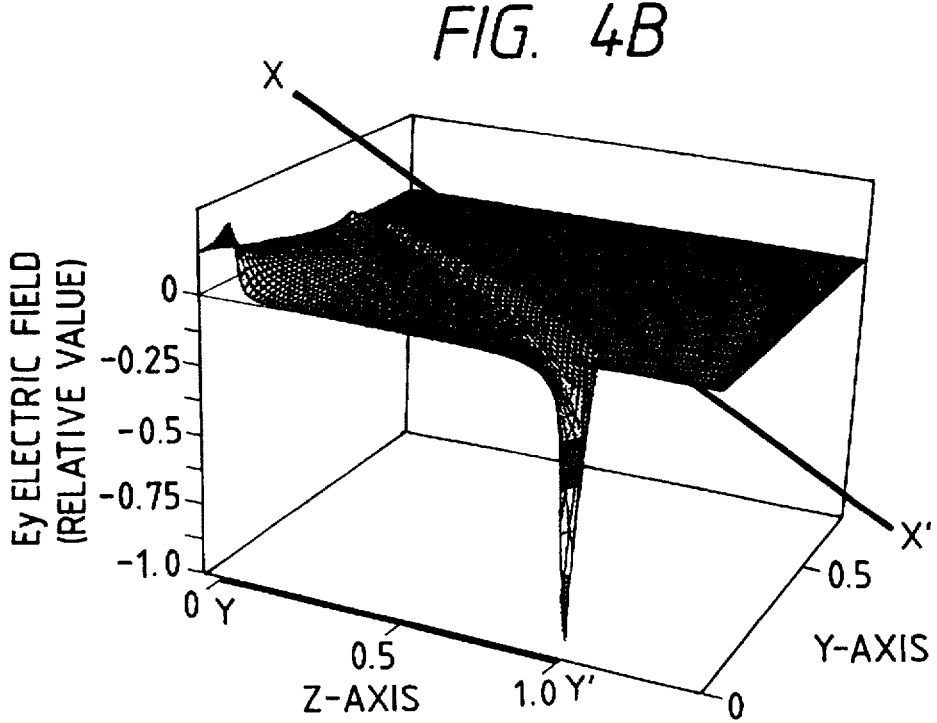
FIG. 4B is a view showing a three dimensional distribution of an electric field (component in a direction of injection of an ion beam) at a deflecting portion of the deflecting and focusing part in the first embodiment of the present invention.

In the embodiment 1 shown in FIG. 1, the inside deflecting electrode 7 is arranged in a direction parallel with that of the injection of the ion beam into the deflecting and focusing part 5, and the outside deflecting electrode 6 is arranged in a slanting direction such that the distance between the electrodes 6 and 7 becomes shorter, as the coordinate in the direction (z direction) of the injection of the ion beam into the deflecting and focusing part 5 becomes larger. The electric field in the deflecting direction (−y direction) becomes stronger, as the coordinate in the direction (z direction) of the injection of the ion beam becomes larger. In other words, a stronger force of the direction (−y direction) of the deflection is exerted on the ion beam as the z coordinate of the ion becomes larger. The result of calculation on a distribution of potentials in the space from the deflecting and focusing part 5 to the ion detecting part 8 is shown in FIG. 2, in which the outside deflecting electrode 6 and the electrodes 16 and 17 connected to the outside deflecting electrode 6 is at the ground potential, the inside deflecting electrode 7 is at a negative potential (−3 kV) (if the ion is positive) (if the ion is negative, it is at a positive potential), and the housing of the ion detector is at the same potential (−3 kV) as that of the inside deflecting electrode 7. The results of calculation on a distribution of the component of −y direction of the electric field generated between the electrodes 6 and 7 are shown in FIGS. 3A and 3B, and the result of calculation on a distribution of z direction of the electric field are shown in FIGS. 4A and 4B. FIGS. 2, 3A, 3B, 4A and 4B shows the results of calculation in the case that the inside deflecting electrode 7 is at a negative potential. The calculation on the potential and the value of the electric field was carried out by using a finite difference method.

It is seen from FIG. 2 that the spacing of equipotential lines between the electrodes 6 and 7 becomes narrow, as the coordinate in the direction (+z direction) of the injection of the ion beam becomes larger.

FIGS. 3A and 4A show distributions of components of y direction and z direction of the electric field in a y–z plane, respectively, obtained by calculating actually the values of the electric fields. FIGS. 3B and 4B are views of the distributions of components of y direction and z direction of the electric field shown in a y–z plane of the three dimensional graph made by adding an axis showing values of relative electric fields, respectively. Where, the origin point of the coordinate is the left end point a of the inside deflecting electrode 7 shown in FIG. 1, the values of the x and y coordinates are indicated by the values relative to the length of the electrode 7, and the value of the electric field is indicated by the value relative to the maximum value of the absolute values of the electric fields. The X–X' and Y–Y' shown in FIGS. 3A, 3B, 4A and 4B indicates the position of the inside deflecting electrode 7. It is seen from FIGS. 3A and 3B that the magnitude of the electric field (deflecting field) in the −y direction increases, as the value of the z coordinate increases. As a result, because the stronger force of the deflection exerts on the ion as the velocity of the ion in the z direction increases, the ion can be deflected with the expansion (dispersion) of the ion beam being suppressed even if the ion beam has the aberration of energy.

It is further seen from FIGS. 4A and 4B that the electric field in the −z direction increases as the value of the z coordinate increases. As a result, the faster the velocity of the ion in the direction of ejection (the larger the energy of the ion), the more the deceleration of the ion in a travelling direction increases. It is, therefore, possible to deflect the ion with the expansion of the ion beam being suppressed. In this case, as shown in FIG. 3, the distribution of the y direction is more effective for the deflection under such a condition that the expansion of the ion beam is suppressed.

The inside deflecting electrode 7 is a mesh electrode made of a lattice or wires. The ion deflected to the position of the inside deflecting electrode 7 can pass through the electrode 7. Therefore, the excess deflecting force does not exert on the ion. As a result, it is possible to prevent the ion with low energy from receiving the excess deflecting force and thus prevent the ion beam from expanding or dispersing.

The focusing portion B of the deflecting and focusing part 5 will be explained next. The characteristics of the focusing portion B according to this embodiment are as follows. By utilizing the fact that ions are separated or dispersed spatially according to respective energy when the ions are deflected at the deflecting portion A, the stronger electric field in the focusing direction is generated in a space where ions with higher energy are distributed, and the weaker electric field in the focusing direction is generated in a space where ions with lower energy are distributed. Further, by generating an extracting electric field in the vicinity of an entrance of the ion detector, the ion beam is focused.

Figure 5:
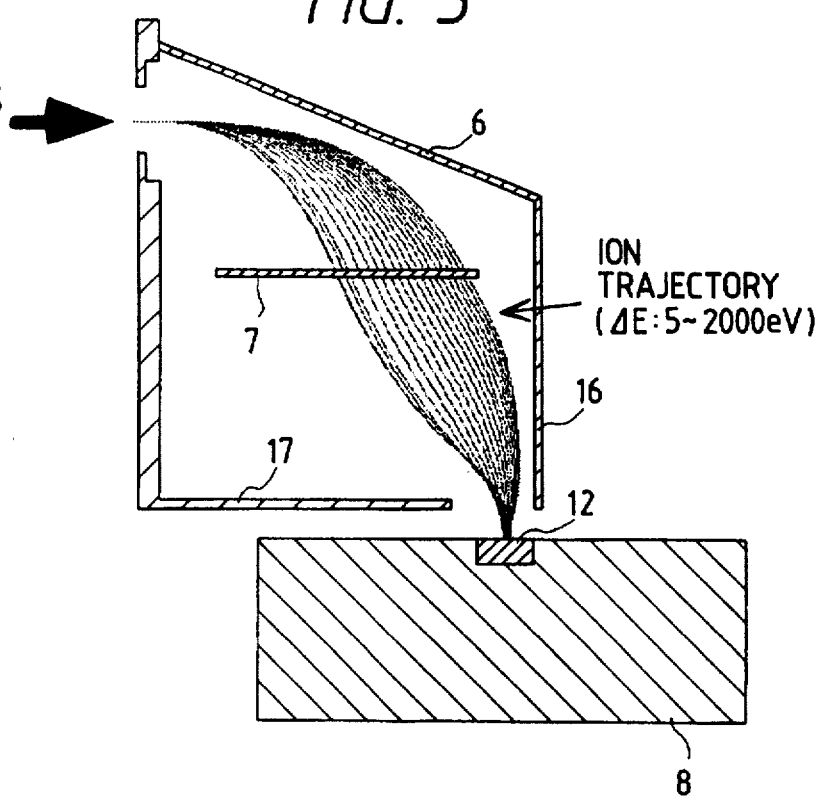
FIG. 5 is a view showing a result of analysis of an ion trajectory from the deflecting and focusing part to a part of the ion detecting part in the first embodiment of the present invention.

In FIG. 5, an electrode 16 connected to the outside deflecting electrode 6 and perpendicular to a z direction is arranged so as to surround the inside deflecting electrode 7. Therefore, an electric field with the large component of a −z direction can be generated (see FIG. 2) in the vicinity of the space (from the neighborhood of the right end b of the inside deflecting electrode 7 to the electrode 16 and along the electrode 16 in FIG. 1) at a large z coordinate where ions with large kinetic energy may pass (see FIG. 5). While, the electric field with the small component of the z direction can be generated (see FIG. 2) in the vicinity of the center of the inside deflecting electrode 7 where ions with low kinetic energy may pass (see FIG. 5). Further, the extracting electric field can be generated at a gap portion having almost the same size as an ion injection port 12 of an ion detector 8, formed between the electrode 16 and the electrode 17 positioned in the vicinity of the ion injection port 12 of the ion detector 8. The ion beam separated or dispersed in energy from those electric field is focused by receiving the force in a direction where the expansion of the ion beam is reduced. Accordingly, since the ion beam can be injected into the injection port 12 of the ion detector 8, it is possible to detect ions with high efficiency.

Figure 22:
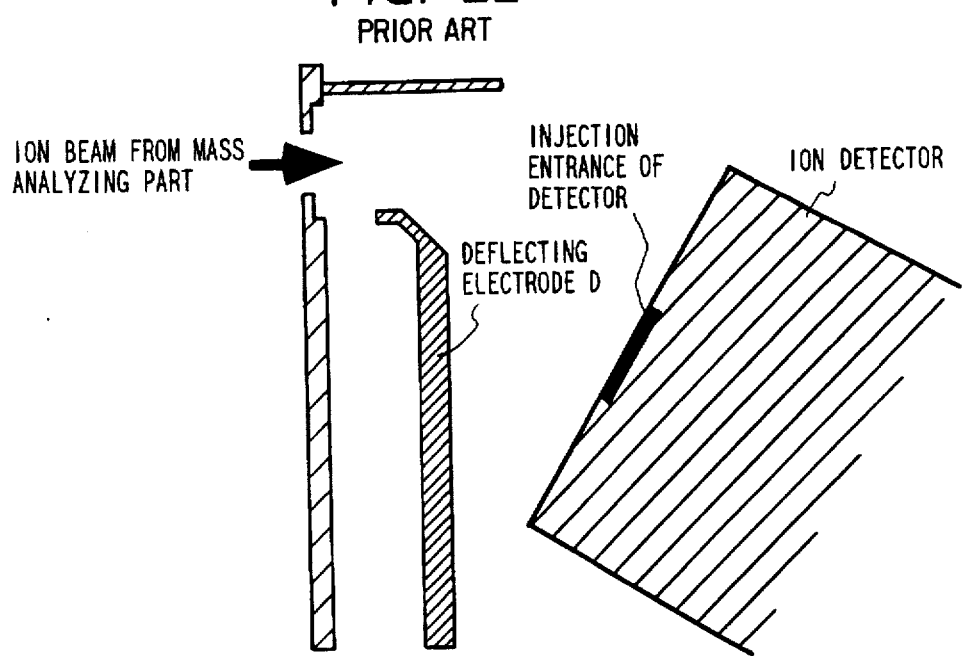
FIG. 22 is a view showing an example 2 of the conventional deflecting electrode device.
Figure 23A:
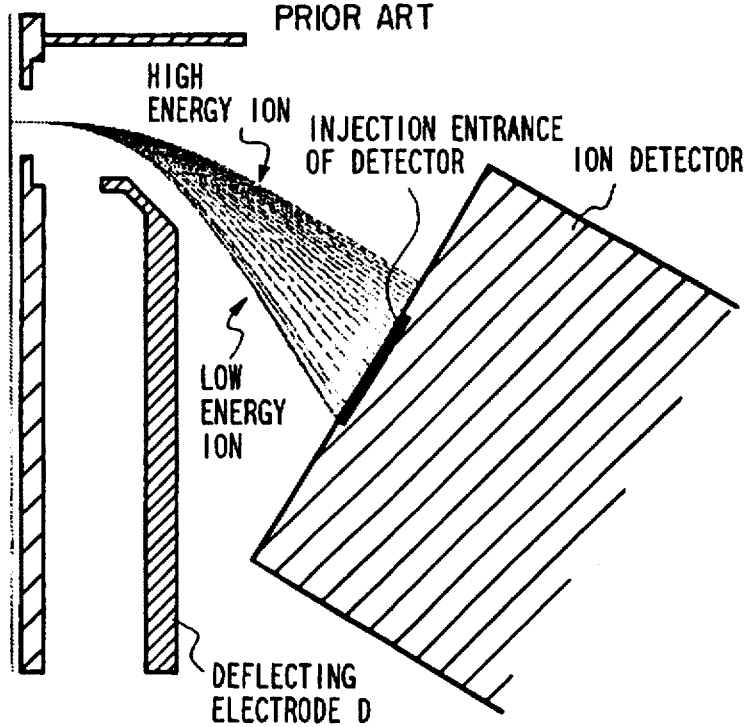
FIG. 23A is a view showing a result of analysis of an trajectory of an ion in the example 2 of the conventional deflecting electrode device.
Figure 23B:
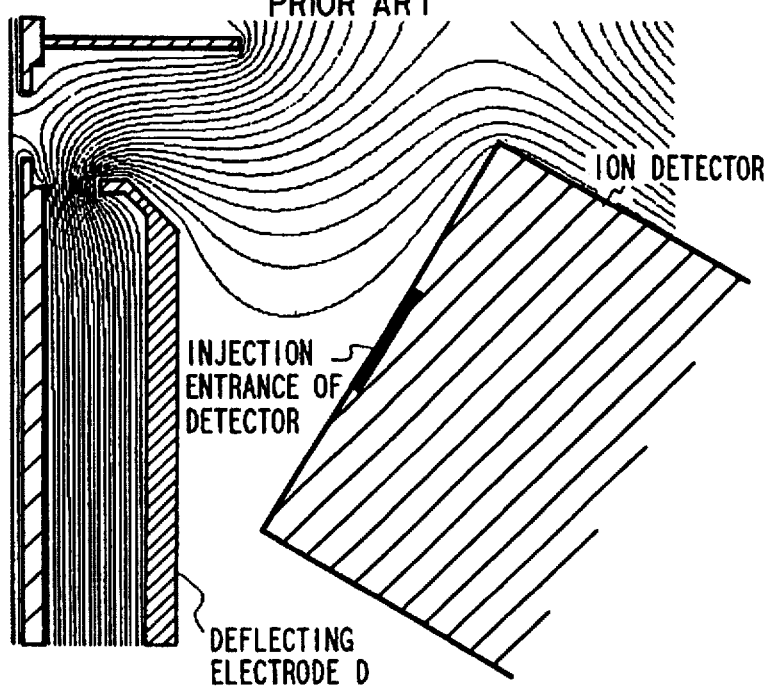
FIG. 23B is a view showing a distribution of potentials in the example 2 of the conventional deflecting electrode device.

FIG. 5 illustrates a result of analysis of an ion trajectory obtained by calculating values of electric potentials and electric fields in a system from the deflecting portion A of the deflecting and focusing part 5 through the focusing portion B to the ion detector, in which a positive ion beam with the energy of 5 to 2000 eV and a mass-to-charge ratio (m/z) of 100 is injected. While, FIGS. 23A and 23B illustrates results of analysis of an ion trajectry and a distribution of an electric potential, in which the conventional deflecting electrode shown in FIG. 22 is used and the same voltage as the inside deflecting electrode 7 of FIG. 1 is applied to a deflecting electrode and a housing of the ion detector. In case that there is a large aberration of energy in the ion beam, the deflecting force decreases (see FIG. 23B) as the energy of an ion increases, namely, the ion travels further into a z direction. Accordingly, In the conventional deflecting electrode of FIG. 23A, the angle of deflection (the angle made by the deflected ion beam with the direction of the ion beam ejected from the mass analyzing part) decreases and the width of the ion beam expands. Referring to FIG. 5, the ion beam which passed through the deflecting and focusing part 5 according to the present embodiment forms a substantially collimated beam after the ion beam is deflected at the deflecting portion A. Accordingly, the ion beam does not expands and experiences an deflecting action. In the focusing part B, the ion with higher energy receives stronger force in the focusing direction or −z direction, and the ion with lower energy receives weaker force in the focusing direction or +z direction. The ion further experiences the focusing action from the extracting electric field generated between the electrodes 16 and 17. Since the ion beam focused sufficiently can be injected into the injection port 12 of the ion detector 8 in the present embodiment, it is possible to detect ions with high efficiency and high sensitivity.

The voltage applied to the inside deflecting electrode 7 and the housing of the ion detector 8 can be adjusted by the control part 10 on the basis of the aberration of the energy of the ion beam predicted from the ratio of charge to mass, that is, the mass number of the ion ejected from the mass analyzing part 4. Even if the aberration of energy increases at this time, it is possible to allow the relationship between the energy of the ion and the distribution of the potential to be relatively identical. As a result, it becomes possible to obtain almost the same ion trajectory.

Figure 6:
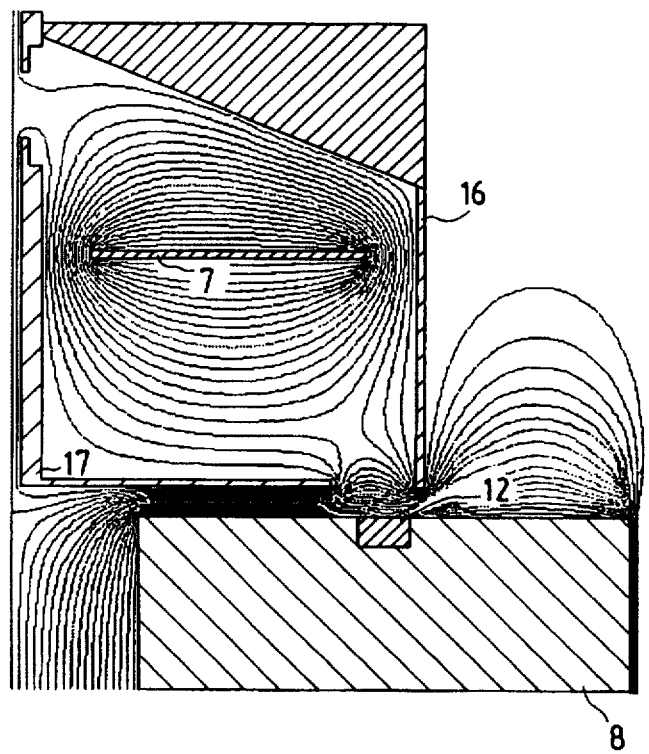
FIG. 6 is a view showing a distribution of potentials from the deflecting and focusing part to a part of the ion detecting part in the first embodiment of the present invention.

The distribution of the electric field generated in the deflecting and focusing part 5 is important for the present invention. It may be possible to change the shape of the outside of the electrode which does not effect on the electric field generated in the deflecting and focusing part 5 if it is possible to obtain a similar distribution of an electric field. For example, it is possible to form the shape of the outside deflecting electrode to be rectangular as shown in FIG. 6. Further, the outside deflecting electrode 6 also may be a mesh electrode like the inside deflecting electrode 7. When the mesh electrode is used, it is possible to prevent the contamination of the electrode, and prevent the neutral molecular gas from staying in the deflecting and focusing part and flowing in a direction of the ion detector.

Embodiment 2

Figure 8A:
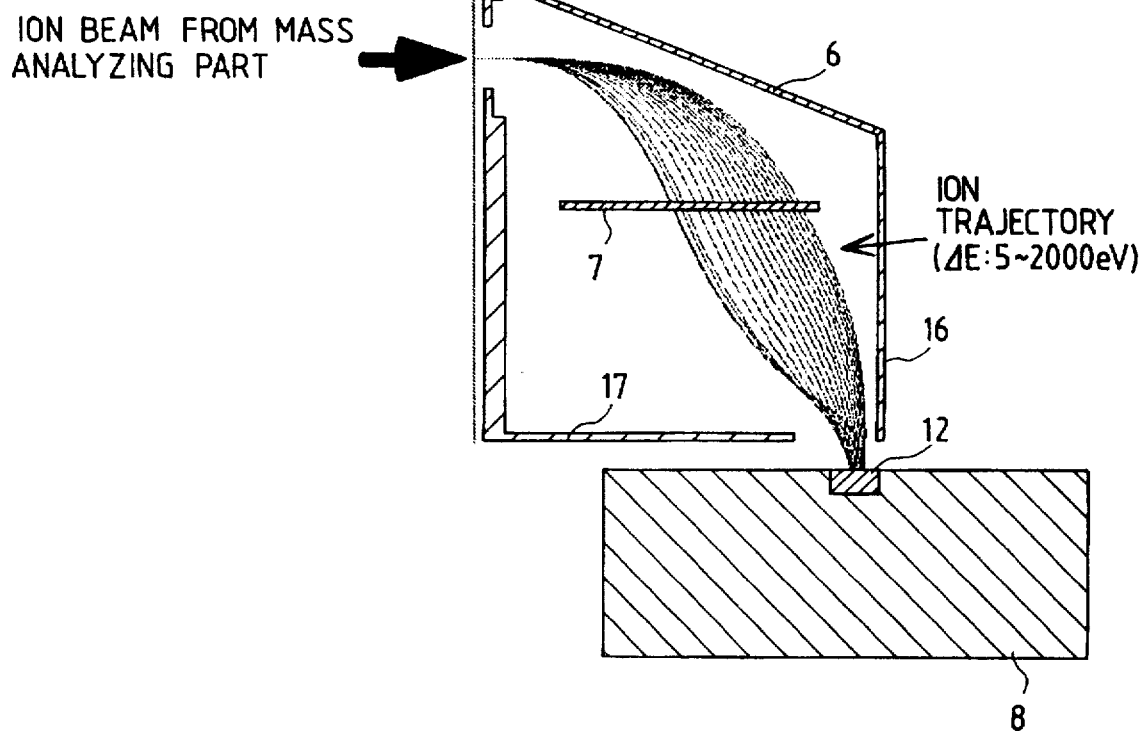
FIG. 8A is a view showing a result of calculation of an trajectory of the ion beam when a voltage is applied in the second embodiment of the present invention.
Figure 8B:
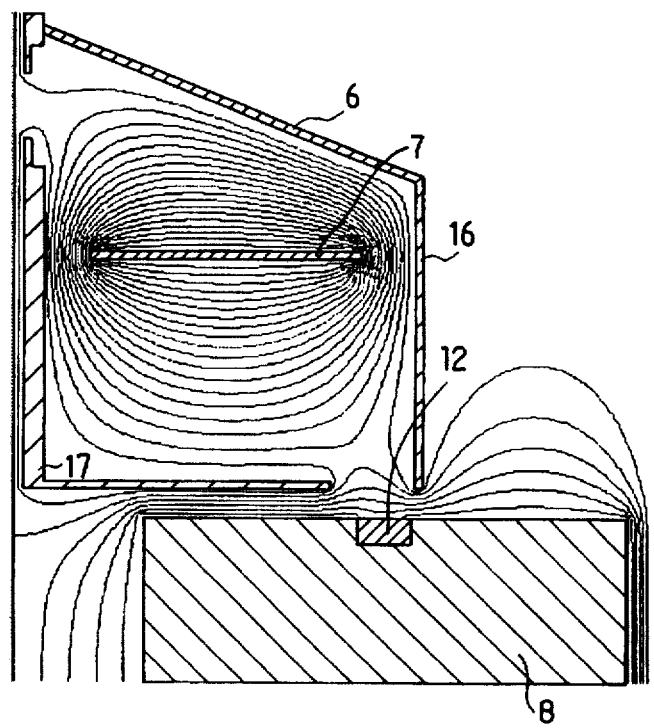
FIG. 8B is a view showing a distribution of potentials when a voltage is applied in the second embodiment of the present invention.

An embodiment 2 will be explained next with reference to FIGS. 7, 8A and 8B. While in the embodiment 1 the same voltage is applied to the inside deflecting electrode 7 and the housing of the ion detector 8, in the embodiment 2, different voltages are applied to them. FIGS. 8A and 8B show results of analysis in such a case that the voltage of −3 kV is applied to the inside deflecting electrode 7 and that of −2 kV to the ion detector 8. In this case, the ion beam deflected by passing between the outside deflecting electrode 6 and the inside deflecting electrode 7, is focused by the extracting electric field generated in the vicinity of the injection port of the ion detector 8, and is injected to the ion detector 8 with high efficiency. Where, it is necessary that the voltage applied to the inside deflecting electrode 7 has such the magnitude that the ion beam having the aberration of energy is not expanded in its width and deflected. While, the voltage applied to the housing of the ion detector 8 has such the magnitude that an extracting electric field can be generated at the gap portion in the vicinity of the injection port of the ion detector between the electrodes 16 and 17. For example, even if the voltage applied to the housing of the ion detector 8 is limited, it is possible to allow the extracting electric field to extend into the deflecting and focusing part 5 by adjusting the magnitude of the gap formed between the electrodes 16 and 17, or the distance between the electrode 17 and the ion detector 8. According to the present embodiment, even if the voltage applied to the housing of the ion detector 8 is limited, it is possible to detect the ion beam having large aberration of energy with high accuracy. It is also possible to increase the degree of focusing of the deflected beam by applying a voltage lower than that of the inside deflecting electrode 7 (if the ion is positive) (if the ion is negative, a voltage higher than that of the inside deflecting electrode 7 is applied).

Embodiment 3

An embodiment 3 will be explained next with reference to FIGS. 9A and 9B. While in the embodiment 1 both the outside deflecting electrode 6 and the inside deflecting electrode 7 are formed by using a plain electrode, in the embodiment 3, either one of them or both of them are formed by using a curved electrode. As shown in FIG. 9A, while the inside deflecting electrode 7 is a plain electrode arranged in parallel with the direction of injection of the ion beam, the outside deflecting electrode 6 is a curved electrode so arranged that the distance between the outside deflecting electrode 6 and the inside deflecting electrode 7 becomes short as the coordinate of the direction (z direction) of injection of the ion beam increases. Because the rate of increase of the electric field in a direction of the deflection (y direction) as compared with the z coordinate is larger than that of the embodiment 1, this configuration is effective when it is desirable to deflect extremely the ion with higher energy.

It should be appreciated that both the inside deflecting electrode 7 and the outside deflecting electrode 6 can be formed by using the curved electrode. Where, the distance between the outside deflecting electrode 6 and the inside deflecting electrode 7 becomes short as the coordinate of the direction (z direction) of injection of the ion beam increases. While in the embodiment 1, the component of the electric field in the −z direction is generated at the region where the value of the z coordinate is large, in the embodiment 3, the component of the electric field in the −z direction (opposite to the direction of injection) is generated in the whole region of the z coordinate. Further, the component of the electric field of the −z direction (a direction opposite to the direction of injection) increases as the value of the z coordinate increases. Accordingly, this embodiment is effective to increase the angle of deflection of the whole ion beam which includes from the ions with lower energy to the ions with higher energy.

Embodiment 4

An embodiment 4 will be explained next with reference to FIGS. 10A and 10B. While in the embodiment 3 either one of the inside deflecting electrode 7 and the outside deflecting electrode 6 or both of them are formed by using a curved electrode, in the embodiment 4, either the outside deflecting electrode 6 or the inside deflecting electrode 7 is formed by combining a plurality of plain electrodes in order to increase the rate of increase of the electric field in a direction (y direction) of the deflection as compared with the z coordinate as in the embodiment 3.

While the inside deflecting electrode 7 of FIG. 10A is a plain electrode arranged in parallel with the direction of the injection of the ion beam as in the embodiment 1, the outside deflecting electrode 6 is formed with two plain electrodes connected to each other with the angles of the plain electrodes being changed with respect to the direction of the injection of the ion beam. Where, the two plain electrodes is connected such that the electrode connected in the down stream of the direction of the ion beam injected into the deflecting portion A has a larger angle of arrangement of the electrode with respect to the direction of the injection of the ion beam than that of the other electrode of the two plain electrodes which form the outside deflecting electrode 6. Because the rate of increase of the electric field in a direction (y direction) of the deflection as compared with the z coordinate is larger, this configuration is effective when it is desirable to deflect extremely the ion with higher energy. Further, because a plurality of plain electrodes are connected with the angles of the electrodes being changed to each other, it is easy to fabricate.

It should be appreciated that a plurality of plain electrodes 6A, 6B and 6C can be arranged in parallel with the direction of the ion beam injected into the deflecting portion A, with the distance between each of the plain electrodes and the inside deflecting electrode 7 being shortened gradually according to the increase of the value of the z coordinate. Because the curved electrode is not used in the embodiment 4, it is easy to fabricate the electrode as compared with the embodiment 3. Further, it is possible to obtain the same effects as the embodiment 3.

Embodiment 5

An embodiment 5 will be explained next with reference to FIG. 11. In the embodiments 1 to 4, by utilizing the fact that ions are separated or dispersed spatially according to respective energy when the ions are deflected at the deflecting portion A, the stronger electric field in the focusing direction is generated in a space where ions with higher energy are distributed, and the weaker electric field in the focusing direction is generated in a space where ions with lower energy are distributed. Further, by generating an extracting electric field in the vicinity of an injection port for the ion detector, the ion beam is focused.

In the present embodiment, electrodes 26 and 27 are arranged in the focusing portion B so that the distribution of electric field can be substantially symmetric like a mirror operation with respect to a plane perpendicular to the collimated ion beam deflected by the deflecting field generated in the deflecting portion A. Hereinafter, these electrodes 26 and 27 are referred to as an outside focusing electrodes and an inside focusing electrode, respectively.

Where, the electrode 27 also is a mesh electrode like the electrode 7. It is not necessary to make the electrodes 26 and 27 of a mesh. However, if the mesh electrode is used for the electrode 26, it is possible to prevent the contamination of the electrode, and prevent the neutral gas from staying in the deflecting and focusing part 5 and flowing in a direction of the ion detector.

In the arrangement of the electrodes of the focusing portion B according to the present embodiment, the distribution of the electric field at the focusing portion B has the following characteristics. The component in the −z direction of the electric field increases as the value of the y coordinate increases, and the component of the z direction of the electric field decreases as it decreases (see FIG. 13B). The ion with lower energy is deflected by the electric field of the deflecting portion A at a portion where the value of the z coordinate is small, and receives the force in the direction along the symmetric plane between the electrodes 7 and 27. And then, it is injected into the electric field generated at a portion where the value of the y coordinate is small in the focusing portion B, and receives the force of the −z direction.

Because the velocity of the ion with higher energy is fast in the z direction, it is deflected at a portion in the deflection portion A where the value of the z coordinate is large. Then, it hardly receives the force, because it pass around the connection portion of the electrodes 7 and 27. However, it is soon injected into the electric field of the focusing portion B at a portion where the value of the y coordinate is large, and receives large force of the −z direction.

Accordingly, the larger the energy of the ion is, the larger the focusing force of the −z direction exerts on the ion, and the smaller the energy of the ion is, the smaller the focusing force of the −z direction exerts on the ion. Because the distribution of electric field is substantially symmetric like a mirror operation with respect to a surface perpendicular to the ion beam deflected in parallel by the deflecting field generated in the deflecting portion A, the ion beam which passes through the electric field also traces the trajectory symmetric like a mirror operation. Accordingly, the ion beam can be focused finely.

Embodiment 6

An embodiment 6 will be explained next with reference to FIGS. 12, 13A, 13B, 14A and 14B. In this embodiment, a multiplier is used as an ion detector, the electrodes are arranged so as to be substantially symmetric like a mirror operation, and the same voltage (−1.3 kV) as a first electrode of the multiplier for generating secondary electrons is applied to the inside deflecting electrode 7, the inside focusing electrode 27 and the housing of the multiplier. Where, in FIG. 13A, the outside deflecting electrode 6, the outside focusing electrode 26 and the electrode 17 are at the ground level (0 V). FIG. 13B shows a result of calculation of the distribution of the electric field for the whole electrode system. FIG. 13A illustrates a result of analysis of an ion trajectory calculated with the result of analysis of FIG. 13B, in which the ion beam having the aberration of energy of 5 to 2000 eV is injected into the deflecting and focusing part 5.

It is seen from FIG. 13A that the ion beam having large aberration of energy can be focused finely after the deflection. Because the same voltage as the first electrode of the multiplier is applied to the inside deflecting electrode 7, the inside focusing electrode 27 and the housing of the multiplier, it is not necessary to provide an additional power source.

Figure 13A:
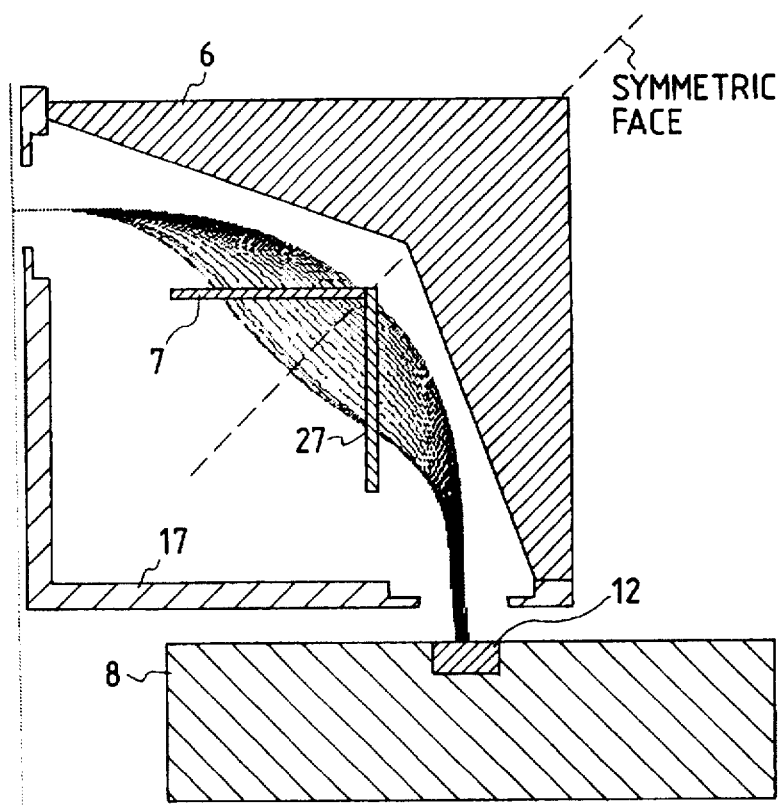
FIG. 13A is a view showing a result of analysis of an ion trajectory from the deflecting and focusing part to a part of the ion detecting part in the sixth embodiment of the present invention.
Figure 13B:
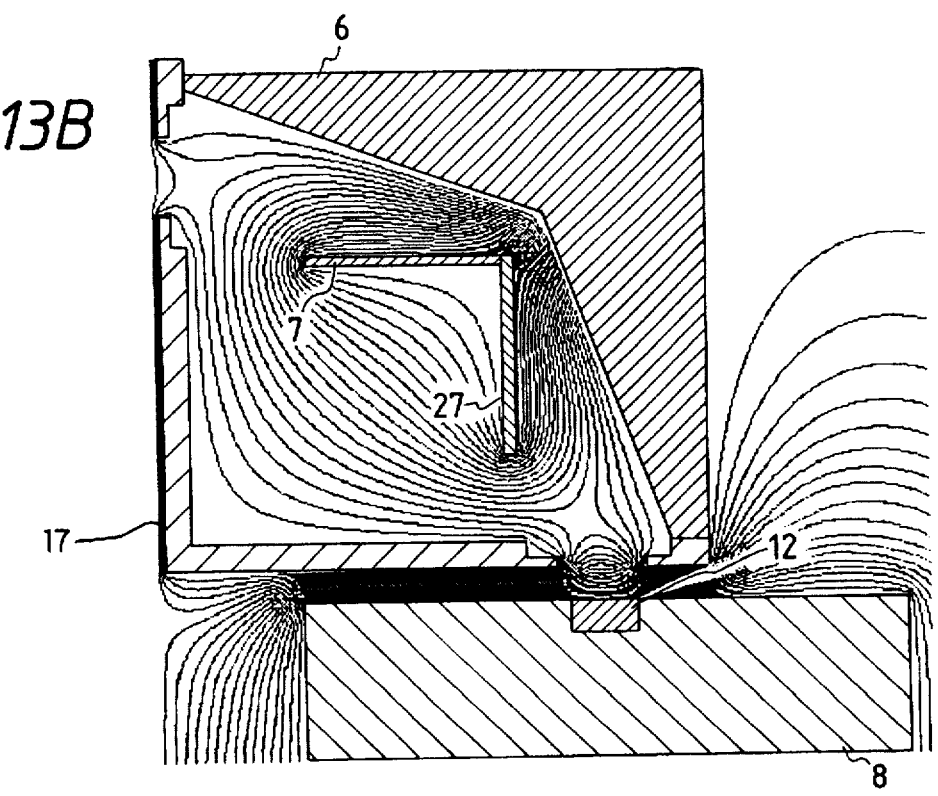
FIG. 13B is a view showing a distribution of potentials from the deflecting and focusing part to the ion detecting part in the sixth embodiment of the present invention.
Figure 14A:
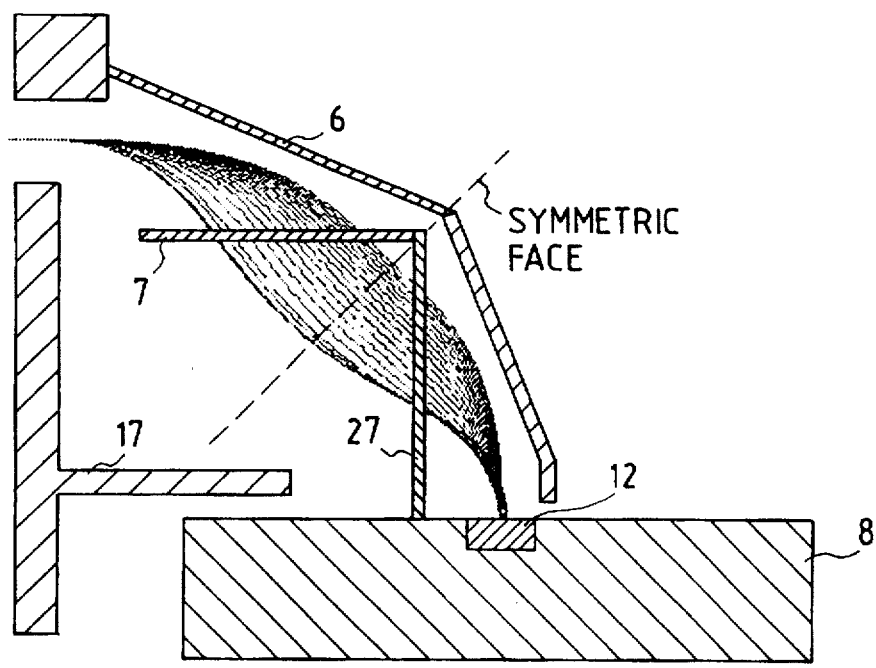
FIG. 14A is a view showing a result of analysis of an ion trajectory from the deflecting and focusing part to a part of the ion detecting part in a modified example of the sixth embodiment of the present invention.
Figure 14B:
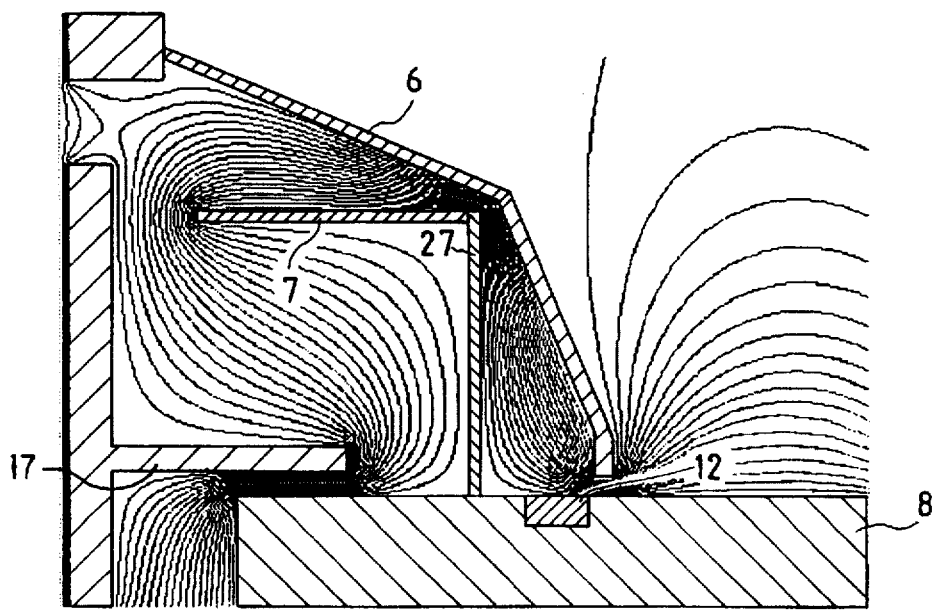
FIG. 14B is a view showing a distribution of potentials from the deflecting and focusing part to the ion detecting part in the modified example of the sixth embodiment of the present invention.

It is not necessary to form the electrodes used in the deflecting and focusing part 5 so as to allow the deflecting portion A to be strictly symmetric with the focusing portion B like a mirror operation. FIG. 14A shows such an example that the deflecting portion A and the focusing portion B are not strictly symmetric with each other like a mirror operation. In FIG. 14A, the length of the y direction of the focusing portion B is shorter than that in the example symmetric like a mirror operation as in FIG. 13A. In addition, the electrode 17 parallel with the z direction and in the vicinity of the multiplier is provided at a position where the value of the y coordinate is larger than the electrode in the example symmetric like a mirror operation. Accordingly, in the example of FIG. 14A, the degree of the symmetry is less than that in the example of FIG. 13 (particularly between the electrodes 7 and 27). FIG. 14B shows a result of calculation of the distribution of the potentials when the same voltage as the example of FIG. 13 is applied to that of FIG. 14A. Further, FIG. 14A shows a result of analysis of the ion trajectory calculated with the result of analysis of FIG. 14B, in which the ion beam having the aberration of energy of 5 to 2000 eV is injected into the deflecting and focusing part 5.

It is seen from these figures that even if the electrodes are out of the symmetric position, it is possible to focus sufficiently the ion beam. Basically, even if the arrangement of the electrodes is not completely symmetric like a mirror operation, it is possible to attain the desired object, by providing the injection port of the ion detector or the multiplier at a position where the ion with higher energy experiences stronger deflecting and focusing force, the ion with lower energy weaker deflecting and focusing force, and thus the width of the ion beam can be narrowed to the maximum. While in this embodiment the arrangement of the electrodes is substantially symmetric like a mirror operation, it is also possible to use the arrangement of the electrodes as described in the embodiments 1 to 4, as the electrodes for the deflecting and focusing part 5. It is desirable to select the type of the electrode in accordance with the space where the deflecting and focusing part 5 and the ion detector or the multiplier are provided.

Embodiment 7

An embodiment 7 will be explained next with reference to FIGS. 15, 16A, 16B, 17A and 17B. Where the housing of the multiplier is set to the ground level in the embodiment 6 of FIG. 12, as shown in FIG. 15, the multiplier is caused to be provided with an aperture 18 having substantially the same size as that of a mesh electrode 20 provided at the entrance portion of the first electrode 14, the aperture 18 being positioned at that portion of the housing of the multiplier onto which the mesh electrode 20 is projected, whereby the ions are made incident on the first electrode 14 through the aperture 18 and then the mesh electrode 20. Because the extracting electric field is generated in the opening portion, ions never bounce back even if the housing of the multiplier is set to the ground level. It is, therefore, possible to detect the ions. If the electrodes substantially symmetric like a mirror operation as shown in FIG. 5 is used as the electrodes for the deflecting and focusing part 5, the same voltage as the first electrode 14 of the multiplier is applied to the inside deflecting electrode 7 and the inside focusing electrode 27, as in the embodiment 6. FIG. 16B shows a result of calculation of the distribution of the potentials in the whole electrode system. Further, FIG. 16A shows a result of analysis of the ion trajectory calculated with the result of analysis of FIG. 16B, in which the ion beam having the aberration of energy of 5 to 2000 eV is injected into the deflecting and focusing part 5.

Figure 16A:
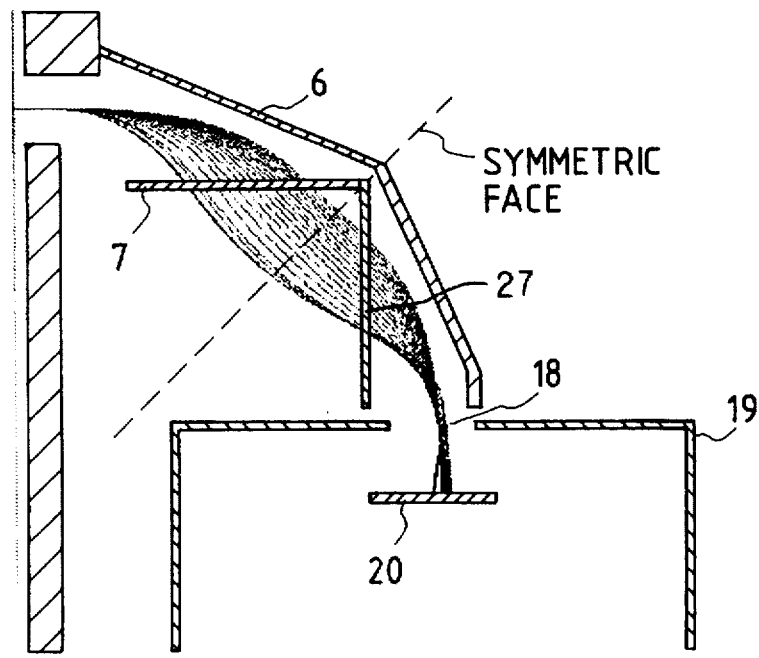
FIG. 16A is a view showing a result of analysis of an ion trajectory from the deflecting and focusing part to a part of the ion detecting part in the seventh embodiment of the present invention.
Figure 16B:
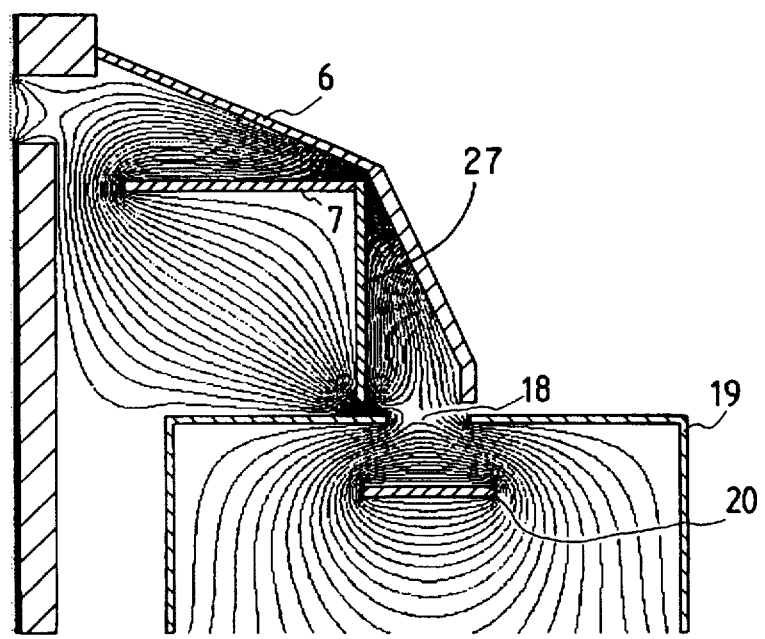
FIG. 16B is a view showing a distribution of potentials from the deflecting and focusing part to the ion detecting part in the seventh embodiment of the present invention.

As is seen from FIG. 16A, because the extracting electric field is generated at the opening portion, the ion beam focused sufficiently after the ion beam with large aberration of energy was deflected, travels to a mesh electrode 20 mounted on the entrance portion of the first electrode 14, without bouncing back. In FIG. 16, only the trajectories to the mesh electrode 20 were calculated, on the assumption that all of the ions which arrived at the mesh electrode 20 pass through the mesh electrode and are detected. Because the same voltage as the first electrode of the multiplier is applied to the inside deflecting electrode 7, the inside focusing electrode 27, it is not necessary to provide an additional power source.

While it has been heretobefore studied on the example (hereinafter, referred to as the vertical arrangement) in which the ion detector 8 is provided in a direction perpendicular to the direction of the ion beam injected into the deflecting and focusing part 5, it is possible to arrange so that the ion detector or the multiplier may be slanted to the direction of the ion beam injected into the deflecting and focusing part 5.

Figure 17A:
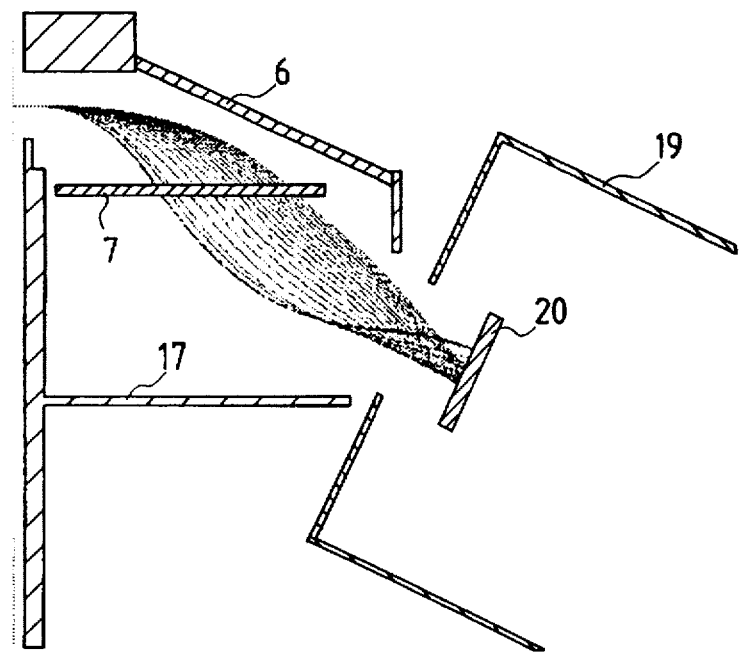
FIG. 17A is a view showing a result of analysis of an ion trajectory from the deflecting and focusing part to the ion detecting part in a modified example of the seventh embodiment of the present invention.
Figure 17B:
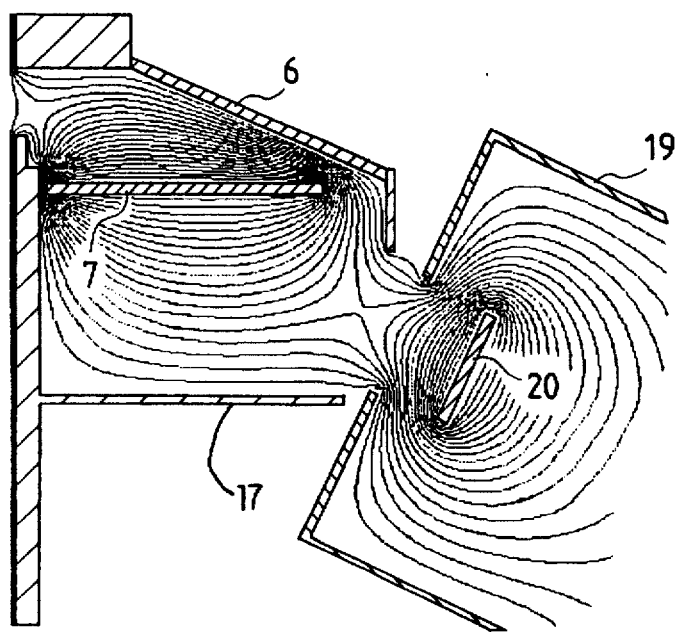
FIG. 17B is a view showing a distribution of potentials from the deflecting and focusing part to the ion detecting part in the modified example of the seventh embodiment of the present invention.

FIG. 17B shows a result of calculation of the distribution of the potentials when the same voltage as the example of FIG. 16 is applied to each of the electrodes. Further, FIG. 17A shows a result of analysis of the ion trajectories calculated with the result of analysis of FIG. 16B, in which the ion beam having the aberration of energy of 5 to 2000 eV and a mass-to-charge ration (m/z) of 100 is injected into the deflecting and focusing part 5. Because in this embodiment the opening portion is directed into a travelling direction of the deflected beam, the ion beam can be focused sufficiently by the extracting electric field generated around the opening portion. It is, therefore, possible to detect the deflected beam with high efficiency.

Further, the deflected beam can be focused sufficiently by the extracting electric field generated around the opening portion, even if there is not provided the electrode 17 in FIG. 17. The result of the calculation proves that the ion beam can be injected into the first electrode with high efficiency. While two examples have been explained, namely, the case that the electrodes for the deflecting and focusing part 5 are substantially symmetric with each other like a mirror operation and the case that the ion detector is slanted as shown in FIG. 17, it is possible to use the arrangement of the electrodes as described in the embodiments 1 to 4. It is possible to select the type of the electrodes in accordance with the space where the deflecting and focusing part 5 and the ion detector 8 or the multiplier are provided.

Embodiment 8

An embodiment 8 will be explained next with reference to FIG. 18. In the embodiment 8, an ion trap type mass analyzer 21 is used as the mass analyzing part 4 shown in the embodiments 1 to 7. The ion trap type mass analyzer 21 comprises a ring electrode 28, and two endcap electrodes 29, 30 positioned so as to face to each other and sandwich the ring electrode 28.

The neutral sample to be mass-analyzed is injected into the space between the electrodes of the ion trap type mass analyzer 21, after the pre-processing part 1 and the moving bed eliminating part 2 in the pre-processing part 1. Then, the neutral sample collides with the electrons injected into the space between the electrodes through a central injection port 31 of the end cap electrode 29 from an electron gun 29 for producing ion, and thus the neutral sample is ionized.

Figure 19:
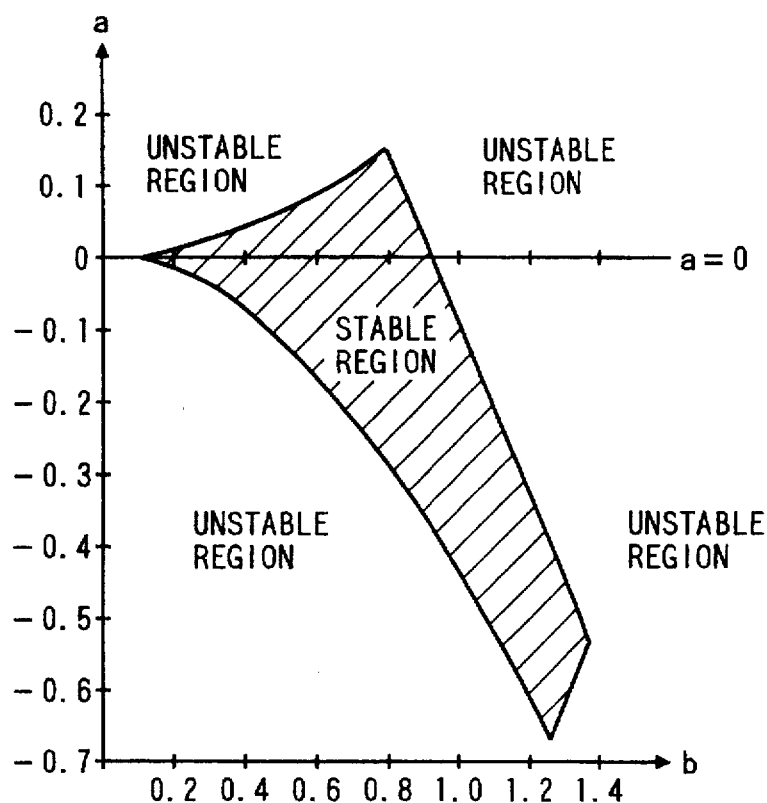
FIG. 19 is a view showing a stable region. a range of (a,q) where an ion travels along a stable trajectory within an ion trap of an ion trap type mass spectrometer.

Whether the ion trajectory is stable or unstable is determined by the coordinate position of the point (a,q) corresponding to the ion, namely, whether the point (a,q) is in a stability region or in an instability region shown in FIG. 19. Where, the trajectory of the ion with the mass-to-charge ratio (m/Z) is in the quadrupole electric field generated in the space between the electrodes by using a high frequency voltage vcos$\Omega$t and a direct-current voltage U which are supplied to between the end cap electrodes 29, 30 and the ring electrode 28 from a main power source for operation 23.

$$a=8eZU/(mr_0^2 \Omega^2), \quad q=4eZV/(mr_0^2 \Omega^2) \qquad (1)$$

where, e designates the quantum of electricity, Z an ionic charge number, the mass-to-charge ratio (m/z) or the mass number, and $r_0$, the inner diameter of the ring electrode.

The magnitude of the voltage supplied from the main power source 23 to the electrodes based on the range of mass-to-charge ratio (i. e., mass range) of the ion to be mass-analyzed is determined in the control system 25 by using the size of the ion trap electrode, the frequency f ($=2\pi\Omega$) of the applied high frequency voltage, etc..

In the present embodiment, as the voltage for operation, the direct current voltage is not applied, but only the high frequency voltage is applied to the ring electrode 28. In FIG. 19, all the ions are stably caught, corresponding to the points within the range of $0 \leq q \leq 0.908$, these being on the straight line of a=0 within the stability region.

As clearly seen from the above equation (1), the q value of the ion and the dominant vibration frequency in the quadruple electric field also are different, when the mass number of the ion (the mass-to-charge ratio (m/Z)) is different. Of the ions stably caught in the ion trap, only the ions with the desired mass-to-charge ratio (m/Z) are picked up and separated according to their m/Z. This is the principle of the ion trap type mass spectrometer.

Mainly, there are the following two methods of picking up only the ion with the desired mass-to-charge ratio (m/Z). 1) the amplitude V of the high frequency voltage applied to the ring electrode is sequentially changed on the basis of the above equation (1). Then, the trajectories of the ions with different mass-to-charge ratio (m/Z) are sequentially made unstable by bringing the point corresponding to each of the ions out of its stability region ($0 \leq q \leq 0.908$ and on the straight line of a=0). As a result, the ion is ejected from the space between the electrodes. (a normal ejection method) 2) A supplementary AC electric field is generated, which has substantially the same frequency as the dominant frequency of the ion with the desired mass-to-charge ratio (m/Z). The amplitude of vibration of the ion with the desired ratio of charge to mass is amplified and the ion is ejected from the space between the electrodes. (a resonant ejection method)

There are known some resonant ejection methods of generating a supplementary AC electric field having substantially the same frequency as the motion frequency of the ion with the desired mass-to-charge ratio (m/Z). The most normal method is as follows. Applied to the end cap electrodes 29 and 30 are the supplementary AC voltages with a specific frequency which are different in phase from each other by 180 degrees. A supplementary electric field which oscillates with a specific period is generated in the space between the quadruple electrodes, in addition to the quadruple electric field. Only the ions with the desired mass-to-charge ratio (m/Z) resonates with the supplementary AC electric field and are ejected from the space between the end cap electrodes and the ring electrode. The amplitude of the main high frequency voltage is scanned, that is, the value q of each of the ion species is scanned by using the above equation (1). Further, the dominant frequency of each of the ion species also is scanned to become closer to the frequency of the supplemental AC voltage. Accordingly, by applying the supplementary AC voltage having a specific frequency and scanning the amplitude of the main high frequency voltage, the mass-to-charge ratio (m/Z) of the resonance-ejected ion is thus scanned. FIG. 18 shows also a power source 24 for applying the supplementary AC voltage.

By the above method, the sequentially mass-analyzed ions exits out of the ion trap type mass analyzer 21 through an ejection port 32 or ion detecting port of the ion trap. The ion beam is ejected along the symmetrical axis of rotation of the ion trap type mass analyzer.

Figure 20A:
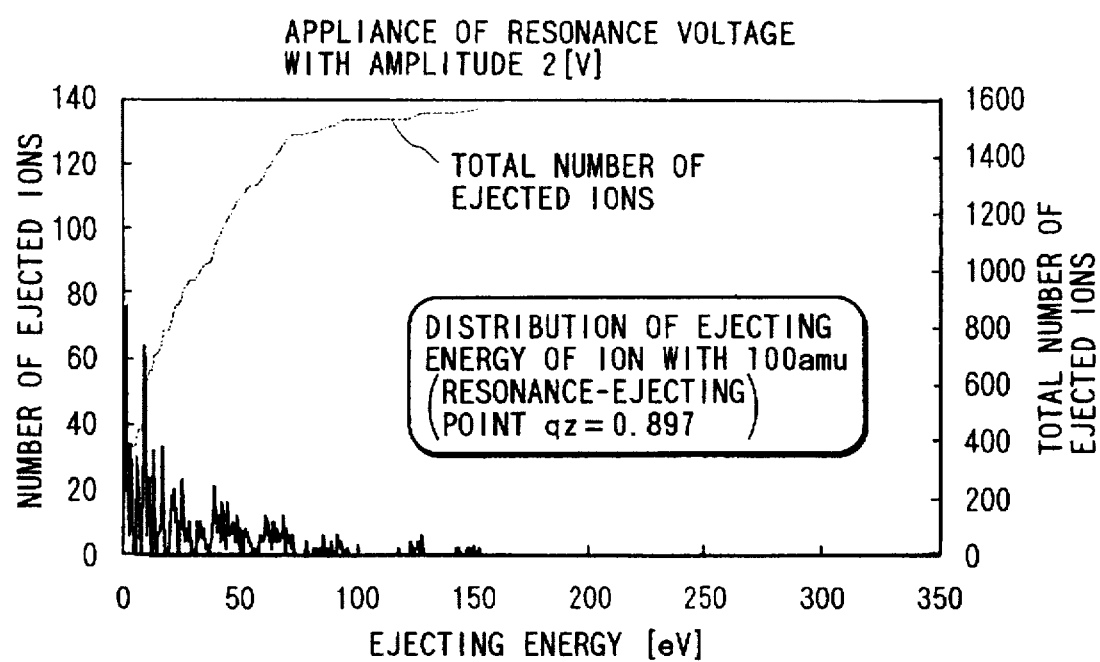
FIG. 20A is a view showing a distribution of energy of singly charged ions with 100 (amu), where a resonance-ejection point is q=0.897 at the time of the ejection from the ion trap, and the amplitude of an applied resonance voltage equals to 2V.

FIGS. 20A, 20B and 20C each shows a result of calculation of the kinetic energy when the ion with 100 (amu) is ejected in resonance, in which the supplementary electric field is generated by applying the resonance voltages with the amplitudes 2V, 10V, 20V to the end cap electrode as shown in FIG. 17, the ion having its ionic charge number 1 and its mass number 100 (amu) and corresponding to the point (a=0, q=0.897) within the stability region. These figures are a distribution diagram for the ejected energy obtained from the calculation on 1550 ions distributed uniformly in the space between the quadruple electrodes. From the distribution diagram, it is understood that the dispersion of large energy occurs when the ion is ejected from the ion trap.

It has been found that the energy dispersion becomes larger as the amplitude of the resonance voltage becomes greater, that is, the energy dispersion at the time of the resonance ejection of the ions depends upon the amplitude of the resonance voltage. The variations in velocity of the ions when they are resonance-ejected hardly depends upon the mass-to-charge ratio (m/Z). It has been proved from the result of calculation that the energy dispersion of the resonance-ejected ions is substantially proportional to the mass-to-charge ratio (m/Z) thereof. Referring to FIG. 20B, assumed that the singly charged ion within the mass range 50 to 650 (amu) is mass-separated by applying the resonance voltage of 10V, the range of the energy dispersion of the ejected ions is about 135.5 eV when the mass of the ion is 50 (amu) and about 1787.5 eV when 650 (amu). Therefore, when the mass-separation is performed within the mass range of 50 to 650 (amu), the total range of the energy dispersion is very large, i.e., approximately 200 ev.

Also in case of the normal ejection, the range of the energy dispersion of the ions is about 30 ev when the mass of the ion singly charged is 100 (amu). It has been understood from the result of calculation that it also is proportional to the mass-to-charge ratio (m/Z).

In a normal two-dimensional quadruple type mass spectrometer, the ion can be injected into the mass analyzing part with almost the same energy regardless of the mass of the ions. Therefore, the energy dispersion is small regardless of the mass of the ion. Further, in a sector type mass spectrometer, normally, double focusing (directional focusing and energy focusing) is performed. Therefore, the width of the energy dispersion is small as in the above case. As seen from the above description, the problem that the width of the energy dispersion becomes large is characteristic of the ion trap type mass spectrometer.

Accordingly, the deflecting and focusing part 5 used in the present invention is very useful when an ion trap type mass analyzer is used for the mass analyzing part 4. In the case, any type of electrodes explained in the embodiments 1 to 6 can be used as the electrodes in the deflecting and focusing part 5. Similarly, any type of ion detector or multiplier can be used.

As understood from the result of calculation shown in FIGS. 20A, 20B and 20C, the degree of the energy dispersion of the ejected ions depends upon the amplitude of the supplementary AC voltage (in case that the ion is resonance-ejected) and the mass-to-charge ratio (m/Z) of the ions. Accordingly, it is possible to determine the magnitude of the voltage applied to the inside deflecting electrode 7 in the control system 10 of FIG. 18, on the basis of the variation in energy corresponding to the mass-to-charge ratio (m/Z) of the ions and the amplitude of the supplementary AC voltage (in case that the ions are resonance-ejected). It should be appreciated that in such the case, the voltage corresponding to the energy dispersion of each ion can be applied to the inside deflecting electrode 7 in accordance with the mass-to-charge ratio (m/Z) to be mass-separated within the mass range and in cooperation with the control system 25 for the ion trap type mass analyzer for controlling the scanning of the ratio of charge to mass of the ion to be mass-analyzed.

The voltage to be applied to the inside deflecting electrode 7 may be determined according to the maximum value of the mass range of the ion to be mass-analyzed. For example, assumed that the mass range for a monovalent positive ion is within the range of 50 through 650 (amu). In this case, such a voltage that the ion having the energy of 1787.5 eV or slightly more, ex. 1800 eV to 2000 eV, is deflected and then effectively focused, is applied to the inside deflecting electrode 7, in consideration that the ejection energy of the ion with 650 (amu) is around 1787.5 eV.

Assumed that the scanning for mass-separating is performed within a predetermined range of the mass-to-charge ratio (m/Z). The magnitude of the voltage to be applied to the inside deflecting electrode 7 can be determined so that the ions with a maximum value of the maximum mass-to-charge ratio (m/Z) in a predetermined range thereof can be deflected, focused and detected with a high efficiency even though such ions have the maximum variation in energy when they are resonance-ejected. If such a voltage is applied to the inside deflecting electrode 7 all through the scanning of the mass-to-charge ratio (m/Z) of the ions to be mass-separated, all the ions within the predetermined range of mass-to-charge ratio (m/Z) can be deflected, focused and detected with a high sensitivity and with a high efficiency without expanding the ion beam. Accordingly, it is not required to adjust the deflecting voltage, etc..

According to the present invention, it is possible to avoid noises due to neutral molecules by detecting the mass-analyzed ions after deflecting them. Further, the expansion of an ion beam due to the energy aberration can be suppressed. Therefore, an improved mass spectrometer can be provided, in which the ion can be detected with a high sensitivity and with a high efficiency.

What is claimed is:

1. A mass spectrometer comprising:
   a. a mass analyzer for mass analyzing ions;
   b. an ion-deflecting-field generator for generating a deflecting field to deflect the mass-analyzed ions, said ion-deflecting-field generator including:
      i. two electrodes facing each other so that the mass-analyzed ions are injected between these electrodes; and
      ii. a power source for applying a potential difference between these electrodes so that the injected ions are deflected to be directed to one of these electrodes, the one electrode being a mesh electrode through which the ions can pass;
   c. an ion focusing device for focusing the deflected ion; and
   d. an ion detector for detecting the focused ions.

2. The mass spectrometer according to claim 1, wherein the other of the two electrodes also is a mesh electrode.

3. The mass spectrometer according to claim 1, wherein the two electrodes have flat surfaces facing each other.

4. The mass spectrometer according to claim 1, wherein the two electrodes have surfaces facing each other, and at least one of the surfaces is a curved surface.

5. The mass spectrometer according to claim 1, wherein at least one of the two electrodes is a combined electrode made by combining a plurality of plates.

6. The mass spectrometer according to claim 1, wherein the ion focusing device generates a focusing field used to focus the deflected ions, and the focusing field is so distributed as to exert on the deflected ions a focusing force which becomes stronger as the energy of ions becomes higher.

7. The mass spectrometer according to claim 1, further comprising an ion extracting field formed at an ion entrance of the ion detector or in the vicinity thereof, which is used to focus the ions from said ion focusing device and make the ions incident on the ion detector.

8. The mass spectrometer according to claim 7, wherein the deflecting field and the focusing field have distributions which are substantially symmetric with respect to a predetermined plane.

9. The mass spectrometer according to claim 7, further comprising a voltage having a magnitude equal to that of the one mesh electrode or a voltage with a polarity opposite to that of the ions, applied to the ion detector to form the ion extracting field.

10. The mass spectrometer according to claim 1, wherein the deflecting field is so distributed that the magnitude of a component thereof in a traveling direction of the ions emitted from the mass analyzer equals zero, or the magnitude of said component gradually increases in a direction of deceleration of the ions as they travel.

11. The mass spectrometer according to claim 1, wherein the ion detector is a multiplier, and further comprising a voltage having a magnitude equal to that of a first electrode of the multiplier applied to the one mesh electrode.

12. The mass spectrometer according to claim 1, wherein said voltage having said magnitude equal to that of said first electrode of the multiplier is applied to a housing of the multiplier.

13. The mass spectrometer according to claim 1, wherein the ion detector is a multiplier, a housing of the multiplier is at the ground potential, and the housing is provided with an ion entrance with the cross-sectional area less than or corresponding to that of a first electrode of the multiplier.

14. The mass spectrometer according to claim 1, wherein the ion detector is so arranged that an ion entrance thereof is located along a direction where the ions travel after being deflected by the deflecting field.

15. The mass spectrometer according to claim 1, wherein the ion detector is so arranged that an ion entrance thereof is directed to a direction perpendicular to a direction in which the ions travels before the ions enter the ion detector.

16. The mass spectrometer according to claim 1, wherein the mass analyzer is of an ion trap in which a three dimensional quadrupole field is formed to trap the ions, and the trapped ions are ejected from the three dimensional quadrupole field according to their mass-to-charge ratio.

17. The mass spectrometer according to claim 1, wherein the ion-deflecting-field generator includes two electrodes facing each other so that the mass-analyzed ions are injected between these electrodes, a potential difference is applied between these electrodes so that the injected ions are deflected to be directed to one of these electrodes, and a three-dimensional quadrupole field is formed to trap the ions, and the trapped ions are ejected from the three dimensional quadrupole field in accordance with their mass-to-charge ratio, the potential difference being determined in accordance with the mass-to-charge ratio of the ions.

18. The mass spectrometer according to claim 1, wherein the ion-deflecting-field generator includes two electrodes facing each other so that the mass-analyzed ions are injected between these electrodes, a potential difference is applied between these electrodes so as that the injected ions can be deflected to be directed to these electrodes, and a three-dimensional quadrupole field is formed to trap the ions, and the trapped ions are ejected from the three dimensional quadrupole field in accordance with their mass-to-charge ratio, and further comprising means for generating a voltage to form a supplementary AC field superimposed upon the three dimensional quadrupole field, the ions are ejected from the three-dimensional quadrupole field in accordance with their mass-to-charge ratio by producing resonance with the supplementary AC field.

19. The mass spectrometer according to claim 1, wherein the ion-deflecting-field generator includes two electrodes facing each other so that the mass-analyzed ions are injected between these electrodes, a potential difference is applied between these electrodes so that the injected ions are deflected to be directed to one of these electrodes, and a three-dimensional quadrupole field is formed to trap the ion, and the trapped ions are ejected from the three-dimensional quadrupole field in accordance with their mass-to-charge ratio, the potential difference being determined in accordance with a maximum one of the mass-to-charge ratios of the ions to be mass-analyzed.

20. The mass spectrometer according to claim 1 wherein the ion-deflecting-field generator includes two electrodes which have inside flat surfaces facing each other so that the mass-analyzed ions are injected between the inside flat surfaces, a space between the inside flat surfaces on a side of injection of the mass-analyzed ions thereinto is narrower than that on an opposite side thereto, and one of the two electrodes is of a mesh electrode to pass the deflected ions therethrough.

21. The mass spectrometer according to claim 20, wherein the ion focusing device includes an electrode connected to said one electrode to extend to said ion detector, and the electrode has an inside flat surface.

22. The mass spectrometer according to claim 20, wherein the ion focusing device includes two electrodes which have inside flat surfaces facing each other and which are electrically connected to the two electrodes of the ion-deflecting-field generator, respectively, wherein a space between the inside flat surfaces of the two electrodes of the ion focusing device on a side of the connection to the two electrodes of the ion-deflecting-field generator is narrower than that on an opposite side, and wherein the electrodes of said ion-deflecting-field generator, is of a mesh electrode to pass the ions passed through the mesh electrode of said ion-deflecting-field generator.

23. The mass spectrometer according to claim 22, wherein both the mesh electrode of said ion-deflecting-field generator and the mesh electrode of said focusing device are connected at a right angle to each other.

24. The mass spectrometer according to claim 23, wherein both the two electrodes of said ion-deflecting-field generator and the two electrodes of said ion focusing device are substantially symmetric with respect to a predetermined plane.

\* \* \* \* \*

UNITED STATES PATENT AND TRADEMARK OFFICE
CERTIFICATE OF CORRECTION

PATENT NO. : 5,756,993
DATED : May 26, 1998
INVENTOR(S) : Kiyomi Yoshinari et al.

It is certified that error appears in the above-identified patent and that said Letters Patent is hereby corrected as shown below:

Column 1, line 1 through Column 15, line 51,
Replace entire text of specification with attached substitute specification Signed and Sealed this Twenty-eighth Day of December, 2004

JON W. DUDAS
*Director of the United States Patent and Trademark Office*

TITLE OF THE INVENTION
Mass Spectrometer

BACKGROUND OF THE INVENTION

The present invention relates to a mass spectrometer, in particular to a mass spectrometer for detecting a mass-analyzed ion, without the occurrence of noises due to a neutral molecular gas.

When a mixture sample is mass-analyzed, it is possible to mass-analyze the mixture sample with a higher degree of accuracy by using a mass spectrometer in which a pre-processing part and a mass-analyzing part are separated from each other. In the pre-processing part, the mixture sample is separated into its components, and in the mass-analyzing part, the mass-to-charge ratio of the separated sample is analyzed. Usually, a gas chromatography or a liquid chromatography is used as the pre-processing part. A new apparatus has recently been developed and put into use, where the pre-processing part and the mass-analyzing part are combined.

In the pre-processing part using the gas chromatography or the liquid chromatography, a mixture sample is flowed to a column packed with a fixed bed, along with a moving bed, that is, a neutral molecular gas (in the gas chromatography) or a solvent (in the liquid chromatography). As a result, the mixture sample can be isolated from the fixed bed due to the difference in affinity. Because the isolated sample still includes the moving bed, it is necessary to eliminate the moving bed in order to mass-analyze the sample. Usually, in the pre-processing part using the liquid chromatography, the solvent is evaporated and then eliminated. Accordingly, in the pre-processing part using either the gas chromatography or the liquid chromatography, the moving bed becomes the neutral gas after the isolation of the sample.

Usually, an eliminating unit for the neutral gas is provided between the pre-processing part and the mass-analyzing part. However, the neutral gas cannot be eliminated completely even through the neutral gas eliminating unit and the pre-processing part pass into the mass-analyzing part. Accordingly, the neutral gas is flowed out of the mass-analyzing part along with the mass-analyzed ion. It is well known that if a detector is provided in a direction of the axis along the direction of ejection of an ion beam from the mass-analyzing part, a noise occurs due to the neutral gas when the mass-analyzed ion is detected. Particularly, in the pre-processing part using the liquid chromatography, the problem of the occurrence of noise is very serious, which occurs due to the neutral molecules of the solvent of the liquid chromatography. Because the amount of neutral gas produced by the evaporation of the solvent is very large as compared to that of the gas chromatography, the detector becomes contaminated by the change of neutral gas into a liquid.

Figure 21:
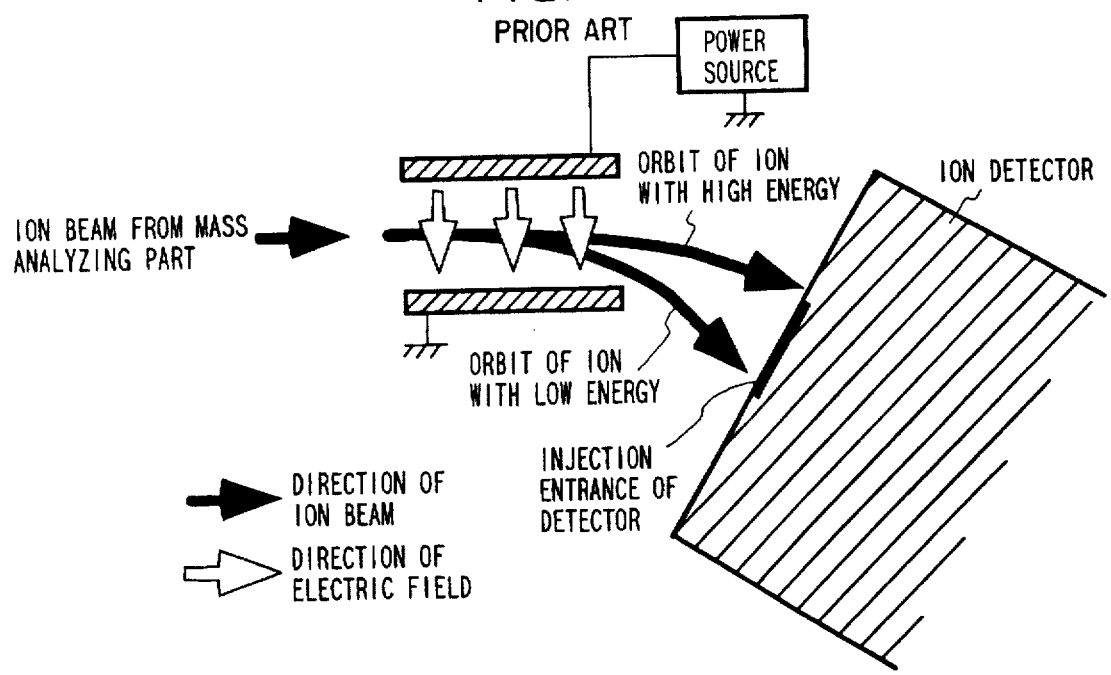
FIG. 21 is a view showing an example 1 of a conventional deflecting electrode device.

Along with conventional and basic methods of deflecting an ion beam, there are other methods, namely, a method of deflecting an ion beam through a constant electric field generated between parallel plates applying the potential difference as shown in Fig.21. Also, a method of deflecting an ion beam through an electric field generated between an electrode bent along a direction of deflection and a plane electrode is shown in Fig.22.

Figs. 23B and 23A show a distribution of potentials and the calculations concerning trajectories of ions having energy aberration within the range from 5 to 2000 eV, respectively, where the conventional deflecting electrodes are arranged as shown in Fig.22. In this example, the ions mass-analyzed are positive with the same negative voltage, 1.4 kV, applied to a deflecting electrode D, a housing of an ion detector, and another electrode located the ground potential.

As clearly seen from these figures, if the ion beam from the mass-analyzing part has aberrant energy the ion beam expands in the deflecting field produced by the conventional deflecting electrodes, and thus the efficiency of detection is deteriorated. This may be caused mainly by the following two facts. (1) The component in a direction of deflection of the electric field generated by the electrodes decreases as the ions travel along a direction of ejection of the ion beam from the mass-analyzing part. Accordingly, because the deflecting force is decreased as the kinetic energy or velocity of the ions in the direction of ejection thereof is increased, the angle of deflection of the ions is decreased and the ion beam expands as the kinetic energy is increased. The angle of deflection indicates an angle made by the ion beam after deflection with the direction of ejection of the ion beam from the mass-analyzing part. (2) The component in a direction of ejection of the ion beam from the mass-analyzing part of the electric field generated by the electrodes increases as the ion travels along a direction of ejection of the ion beam from the mass-analyzing part. Accordingly, the ions with higher energy or higher velocity ions in a direction of ejection are accelerated more in a direction of acceleration of the ions. Accordingly, the angle of deflection of the ions with higher energy becomes smaller and the width of the ion beam becomes wider.

SUMMARY OF THE INVENTION

The present invention is to provide a mass spectrometer which can avoid noises due to neutral molecules by deflecting and detecting the mass-analyzed ions.

The present invention is to provide a mass spectrometer which can avoid noises due to neutral molecules by deflecting and detecting the mass-analyzed ion, and which can suppress the expansion of an ion beam caused by energy aberration of the mass-analyzed ions, wherein it is possible to detect the ions with a higher efficiency and with a higher sensitivity.

In a mass spectrometer according to the present invention, ions are mass-analyzed by a mass analyzer, the mass-analyzed ions are deflected by an ion deflecting device, the deflected ions are focused by a focusing device, and the focused ions are detected by an ion detector.

While the mass-analyzed ions are detected after being deflected by the ion deflecting device, the neutral molecule cannot be deflected by the ion deflecting device because of its neutrality. As a result, noises due to the neutral molecules can be avoided.

When the mass-analyzed ions have energy aberration, the ions are dispersed by the ion deflecting device in accordance with the magnitude of its energy. However, the expansion of the ion beam can be suppressed by the ion focusing device, because the dispersed ion beam is focused by the ion focusing device. As a result, the mass-analyzed ions can be detected with a higher degree of efficiency and with a higher sensitivity.

In the present invention, a stronger power of deflection is provided as the energy of an ion becomes higher. Accordingly, the expansion of the ion beam due to its dispersion caused while the ions travel in the deflecting device can be suppressed more, because the degree of dispersion of the dispersed ions is suppressed by the force of deflection. Additionally, the dispersed ions are focused by the ion focusing device.

Other advantages of this invention will clearly appear from the description and from the accompanying drawings.

BRIEF DESCRIPTION OF THE DRAWINGS

Fig. 1 is a schematic view showing the complete mass spectrometer according to a first embodiment of the present invention.

Fig. 2 is a sectional view of a part of an ion detecting part and a deflecting and focusing part in the first embodiment of the present invention.

Fig. 3A is a view showing a two-dimensional distribution of an electric field (component in a direction of deflection) at a deflecting portion of the deflecting and focusing part in the first embodiment of the present invention.

Fig. 3B is a view showing a three-dimensional distribution of an electric field (component in a direction of deflection) at a deflecting portion of the deflecting and focusing part in the first embodiment of the present invention.

Fig. 4A is a view showing a two-dimensional distribution of an electric field (component in a direction of injection of an ion beam) at a deflecting portion of the deflecting and focusing part in the first embodiment of the present invention.

Fig. 4B is a view showing a three-dimensional distribution of an electric field (component in a direction of injection of an ion beam) at a deflecting portion of the deflecting and focusing part in the first embodiment of the present invention.

Fig. 5 is a view showing a result of analysis of an ion trajectory from the deflecting and focusing part to a part of the ion detecting part in the first embodiment of the present invention.

Fig. 6 is a view showing a distribution of potentials from the deflecting and focusing part to a part of the ion detecting part in the first embodiment of the present invention.

Fig. 7 is a schematic view showing the whole mass spectrometer according to a second embodiment of the present invention.

Fig. 8A is a view showing a result of calculation of a trajectory of the ion beam when a voltage is applied in the second embodiment of the present invention.

Fig. 8B is a view showing a distribution of potentials when a voltage is applied in the second embodiment of the present invention.

Fig. 9A is a sectional view of deflecting electrodes of a mass spectrometer according to a third embodiment of the present invention.

Fig. 9B is a sectional view of a modified example of the deflecting electrodes of the mass spectrometer according to the third embodiment of the present invention.

Fig. 10A is a sectional view of deflecting electrodes of a mass spectrometer according to a fourth embodiment of the present invention.

Fig. 10B is a sectional view of a modified example of the deflecting electrodes of the mass spectrometer according to the fourth embodiment of the present invention.

Fig. 11 is a sectional view showing the deflecting and focusing part of the mass spectrometer according to the fifth embodiment of the present invention.

Figure 12:
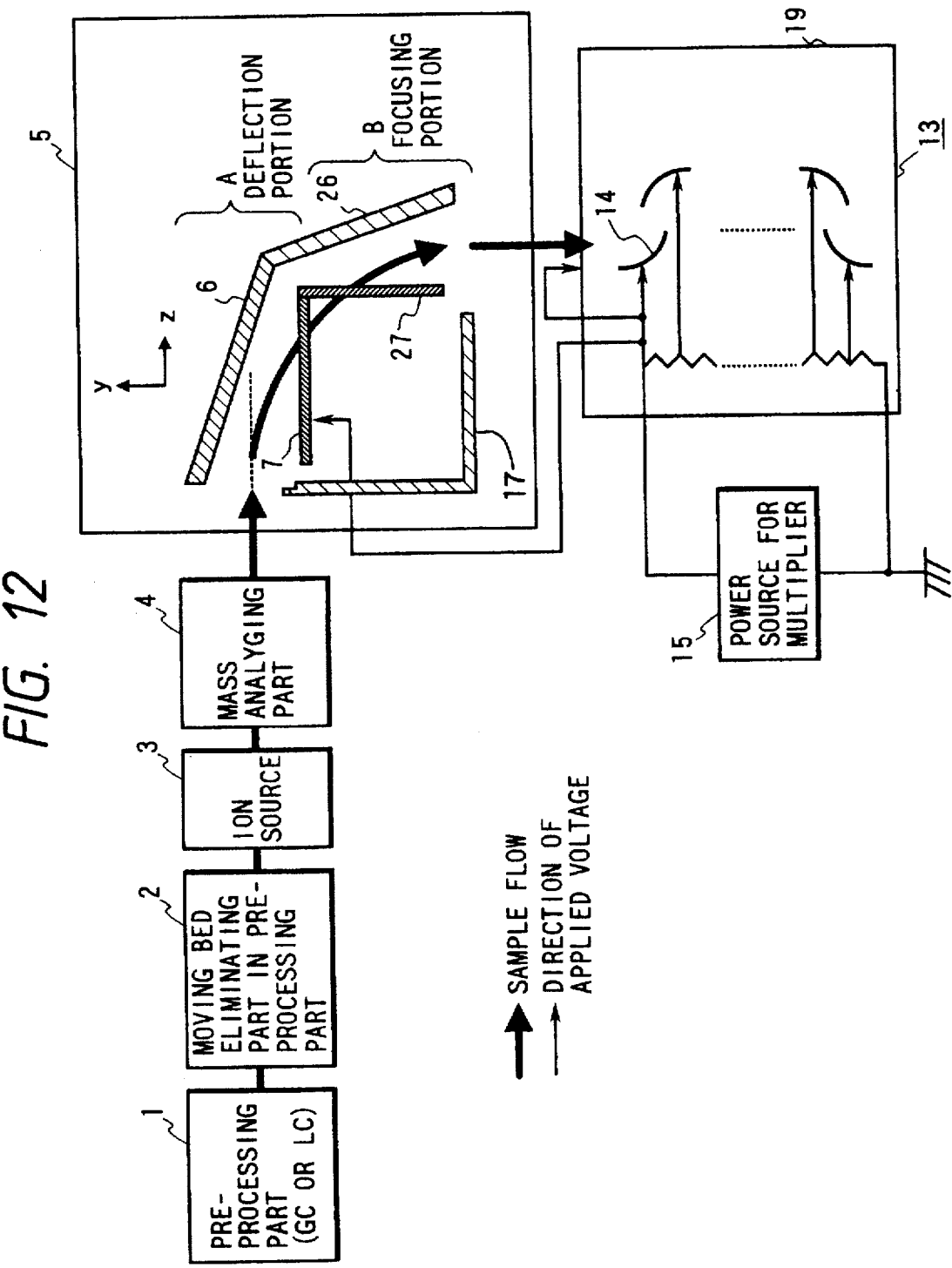
FIG. 12 is a schematic view showing the whole mass spectrometer according to a sixth embodiment of the present invention.

Fig. 12 is a schematic view showing the whole mass spectrometer according to a sixth embodiment of the present invention.

Fig. 13A is a view showing a result of analysis of an ion trajectory from the deflecting and focusing part to a part of the ion detecting part in the sixth embodiment of the present invention.

Fig. 13B is a view showing a distribution of potentials from the deflecting and focusing part to the ion detecting part in the sixth embodiment of the present invention.

Fig. 14A is a view showing a result of analysis of an ion trajectory from the deflecting and focusing part to a part of the ion detecting part in a modified example of the sixth embodiment of the present invention.

Fig. 14B is a view showing a distribution of potentials from the deflecting and focusing part to the ion detecting part in the modified example of the sixth embodiment of the present invention.

Fig. 15 is a schematic view showing the whole mass spectrometer according to a seventh embodiment of the present invention.

Fig. 16A is a view showing a result of analysis of an ion trajectory from the deflecting and focusing part to a part of the ion detecting part in the seventh embodiment of the present invention.

Fig. 16B is a view showing a distribution of potentials from the deflecting and focusing part to the ion detecting part in the seventh embodiment of the present invention.

Fig. 17A is a view showing a result of analysis of an ion trajectory from the deflecting and focusing part to the ion detecting part in a modified example of the seventh embodiment of the present invention.

Fig. 17B is a view showing a distribution of potentials from the deflecting and focusing part to the ion detecting part in the modified example of the seventh embodiment of the present invention.

Fig. 18 is a schematic view showing the entire mass spectrometer according to an eighth embodiment of the present invention.

Fig. 19 is a view showing a stable region, a range of (a,q) where an ion travels along a stable trajectory within an ion trap of an ion trap type mass spectrometer.

Fig. 20A is a view showing a distribution of energy of singly charged ions with 100 (amu), where a resonance-ejection point is q = 0.897 at the time of the ejection from the ion trap, and the amplitude of an applied resonance voltage equals 2V.

Fig. 20B is a view showing a distribution of energy of singly charged ions with 100 (amu), where a resonance-ejection point is q = 0.897 at the time of the ejection from the ion trap, and the amplitude of an applied resonance voltage equals 10V.

Fig. 20C is a view showing a distribution of energy of singly charged ions with 100 (amu), where a resonance-ejection point is q = 0.897 at the time of the ejection from the ion trap, and the amplitude of an applied resonance voltage equals 20V.

Fig. 21 is a view showing an example 1 of a conventional deflecting electrode device.

Fig. 22 is a view showing an example 2 of the conventional deflecting electrode device.

Fig. 23A is a view showing a result of analysis of a trajectory of an ion in the example 2 of the conventional deflecting electrode device.

Fig. 23B is a view showing a distribution of potentials in the example 2 of the conventional deflecting electrode device.

DETAILED DESCRIPTION

A first embodiment will be explained with reference to Fig.1 through Fig.6. Fig.1 is a schematic view showing the complete mass spectrometer according to the first embodiment of the present invention. A mixture sample to be mass-analyzed is separated into its components through a pre-processor part 1 which comprises a gas chromatography (GC) or a liquid chromatography (LC). Then, a moving bed of the sample from the pre-processing part is eliminated by using a moving bed eliminating part. The sample is ionized by an ion source 3 and mass-analyzed by a mass-analyzing part 4. The mass-analyzed ion is deflected and focused by a deflecting portion A and a focusing portion B, respectively, in a deflecting and focusing part 5, and is detected by an ion detecting part 8. The result of detection is processed by a data processing part 11. The deflecting and focusing part 5 comprises the deflecting portion A for deflecting the ion beam and the focusing portion B for focusing the deflected ion beam.

The deflecting portion A will be explained next. In order for the ions to receive a force in a direction (-y direction) to be deflected, a potential difference is applied between electrodes 6 and 7 -- thereby a deflecting field is generated in a space formed between the electrodes 6 and 7 which is arranged to sandwich the ion beam injected into the deflecting and focusing part 5 in the y direction. The electrode 7 is referred to hereinafter as an inside deflecting electrode, positioned at a side to which the ion is deflected, and the electrode 6 opposite to the electrode 7 is referred to as an outside deflecting electrode.

In the first embodiment shown in Fig. 1, the inside deflecting electrode 7 is arranged in a direction parallel with that of the injection of the ion beam into the deflecting and focusing part 5, and the outside deflecting electrode 6 is arranged in a slanting direction such that the distance between electrodes 6 and 7 becomes shorter, as the coordinate in the direction (z direction) of the injection of the ion beam into the deflecting and focusing part 5 becomes larger. The electric field in the deflecting direction (-y direction) becomes stronger, as the coordinate in the direction (z direction) of the injection of the ion beam becomes larger. In other words, a stronger force of the direction (-y direction) of the deflection is exerted on the ion beam as the z coordinate of the ion becomes larger. The calculation of a distribution of potentials in the space from the deflecting and focusing part 5 to the ion detecting part 8 is shown in Fig.2, in which the outside deflecting electrode 6 and the electrodes 16 and 17 connected to the outside deflecting electrode 6 are at the ground potential, the inside deflecting electrode 7 is at a negative potential (-3 kV) (if the ion is positive) (if the ion is negative, it is at a positive potential), and the housing of the ion detector is at the same potential (-3 kV) as that of the inside deflecting electrode 7. The calculations of a distribution of the component in the -y direction of the electric field generated between the electrodes 6 and 7 are shown in Figs. 3A and 3B, and the calculations of a distribution in the z direction of the electric field are shown in Figs. 4A and 4B. Figs. 2, 3A, 3B, 4A and 4B show the calculations where the inside deflecting electrode 7 is at a negative potential. The calculation of the potential and the value of the electric field was carried out by using a finite difference method.

It is seen from Fig. 2 that the spacing of equipotential lines between the electrodes 6 and 7 becomes narrow, as the coordinate in the direction (+z direction) of the injection of the ion beam becomes larger.

Figs. 3A and 4A show distributions of components in the y direction and z direction of the electric field in a y-z plane, respectively, obtained by actually calculating the values of the electric fields. Figs. 3B and 4B are views of the distributions of components in the y direction and z direction of the electric field shown in a y-z plane of the three-dimensional graph made by adding an axis showing values of relative electric fields, respectively. The origin of the coordinate is the left end point $a$ of the inside deflecting electrode 7 shown in Fig. 1, the values of the x and y coordinates are indicated by the values relative to the length of the electrode 7, and the value of the electric field is indicated by the value relative to the maximum value of the absolute values of the electric fields. The X-X' and Y-Y' shown in Figs. 3A, 3B, 4A and 4B indicate the position of the inside deflecting electrode 7. It is seen from Figs. 3A and 3B that the magnitude of the electric field (deflecting field) in the -y direction increases as the value of the z coordinate increases.

Because a stronger force of deflection is exerted on the ions as the velocity of the ions in the z direction increases, the ions can be deflected with the expansion (dispersion) of the ion beam being suppressed even if the ion beam has an aberration of energy.

It is further seen from Figs. 4A and 4B that the electric field in the -z direction increases as the value of the z coordinate increases. As a result, the faster the velocity of the ions in the direction of ejection (the larger the energy of the ions), the more the deceleration of the ions in a traveling direction increases. It is, therefore, possible to deflect the ions with the expansion of the ion beam being suppressed. In this case, as shown in Figs. 3A and 3B, the distribution in the y direction is more effective for the deflection under such a condition that the expansion of the ion beam is suppressed.

The inside deflecting electrode 7 is a mesh electrode made of a lattice or wires. The ions deflected to the position of the inside deflecting electrode 7 can pass through the electrode 7. Therefore, the excess deflecting force is not exerted on the ions. As a result, it is possible to prevent ions with low energy from receiving the excess deflecting force and thus prevent the ion beam from expanding or dispersing.

The focusing portion B of the deflecting and focusing part 5 will be explained next. The characteristics of the focusing portion B according to this embodiment are as follows. By utilizing the fact that ions are separated or dispersed spatially according to their respective energies when the ions are deflected at the deflecting portion A, the stronger electric field in the focusing direction is generated in a space where ions with higher energy are distributed, and the weaker electric field in the focusing direction is generated in a space where ions with lower energy are distributed. Further, by generating an extracting electric field in the vicinity of an entrance of the ion detector, the ion beam becomes focused.

In Fig. 5, an electrode 16 connected to the outside deflecting electrode 6 and perpendicular to the z direction is arranged so as to surround the inside deflecting electrode 7. Therefore, an electric field with the large component in a -z direction can be generated (see Fig. 2) in the vicinity of the space (from the neighborhood of the right end b of the inside deflecting electrode 7 to the electrode 16 and along the electrode 16 in Fig. 1) at a large z coordinate where ions with large kinetic energy may pass (see Fig. 5), while an electric field with the small component in the z direction can be generated (see Fig. 2) in the vicinity of the center of the inside deflecting electrode 7 where ions with low kinetic energy may pass (see Fig. 5). Further, the extracting electric field can be generated at a gap portion having almost the same size as an ion injection port 12 of an ion detector 8, formed between the electrode 16 and the electrode 17 positioned in the vicinity of the ion injection port 12 of the ion detector 8. The ion beam separated or dispersed in energy from those electric fields is focused by receiving the force in a direction where the expansion of the ion beam is reduced. Accordingly, since the ion beam can be injected into injection port 12 of the ion detector 8, it is possible to detect ions with high efficiency.

Fig. 5 illustrates a result of an analysis of an ion trajectory obtained by calculating values of electric potentials and electric fields in a system from the deflecting portion A of the deflecting and focusing part 5 through the focusing portion B to the ion detector, in which a positive ion beam with the energy of 5 to 2000 eV and a mass-to-charge ratio (m/z) of 100 is injected. Figs. 23A and 23B illustrate results of an analysis of an ion trajectory and a distribution of an electric potential, in which the conventional deflecting electrode shown in Fig. 22 is used and the same voltage as the inside deflecting electrode 7 of Fig. 1 is applied to a deflecting electrode and a housing of the ion detector. In case there is a large aberration of energy in the ion beam, the deflecting force decreases (see Fig.23B) as the energy of an ion increases, namely, the ion travels further into a $z$ direction. Accordingly, in the conventional deflecting electrode of Fig. 23A, the angle of deflection (the angle made by the deflected ion beam with the direction of the ion beam ejected from the mass analyzing part) decreases and the width of the ion beam expands. Referring to Fig. 5, the ion beam which passed through the deflecting and focusing part 5 according to the present embodiment forms a substantially collimated beam after the ion beam is deflected at the deflecting portion A. Accordingly, the ion beam does not expand and experiences a deflecting action.

In the focusing part B, the ion with higher energy receives stronger force in the focusing direction or -z direction, and the ion with lower energy receives weaker force in the focusing direction or +z direction. The ion further experiences the focusing action from the extracting electric field generated between the electrodes 16 and 17. Since the ion beam focused sufficiently can be injected into the injection port 12 of the ion detector 8 in the present embodiment, it is possible to detect ions with high efficiency and high sensitivity.

The voltage applied to the inside deflecting electrode 7 and the housing of the ion detector 8 can be adjusted by the control part 10 on the basis of the aberration of the energy of the ion beam predicted from the ratio of charge to mass, that is, the mass number of the ion ejected from the mass analyzing part 4. Even if the aberration of energy increases at this time, it is possible to allow the relationship between the energy of the ion and the distribution of the potential to be relatively identical. As a result, it becomes possible to obtain almost the same ion trajectory.

The distribution of the electric field generated in the deflecting and focusing part 5 is important for the present invention. It may be possible to change the shape of the outside of the electrode which does not affect the electric field generated in the deflecting and focusing part 5 if it is possible to obtain a similar distribution of an electric field. For example, it is possible to form the shape of the outside deflecting electrode to be rectangular as shown in Fig.6. Further, the outside deflecting electrode 6 also may be a mesh electrode like the inside deflecting electrode 7. When the mesh electrode is used, it is possible to prevent the contamination of the electrode, and prevent the neutral molecular gas from staying in the deflecting and focusing part and flowing in a direction of the ion detector.

A second embodiment will be explained next with reference to Figs.7, 8A and 8B. While in the first embodiment the same voltage is applied to the inside deflecting electrode 7 and the housing of the ion detector 8, in the second embodiment, different voltages are applied to them. Figs. 8A and 8B show results of an analysis in such a case where the voltage of -3 kV is applied to the inside deflecting electrode 7 and that of -2kV to the ion detector 8. In this case, the ion beam deflected by passing between the outside deflecting electrode 6 and the inside deflecting electrode 7 is focused by the extracting electric field generated in the vicinity of the injection port of the ion detector 8, and is injected to the ion detector 8 with high efficiency. While it is necessary that the voltage applied to the inside deflecting electrode 7 has such a magnitude that the ion beam having the aberration of energy is not expanded in its width and deflected, the voltage applied to the housing of the ion detector 8 must have such magnitude that an extracting electric field can be generated at the gap portion in the vicinity of the injection port of the ion detector between the electrodes 16 and 17. For example, even if the voltage applied to the housing of the ion detector 8 is limited, it is possible to allow the extracting electric field to extend into the deflecting and focusing part 5 by adjusting the magnitude of the gap formed between the electrodes 16 and 17, or the distance between the electrode 17 and the ion detector 8.

According to the present embodiment, even if the voltage applied to the housing of the ion detector 8 is limited, it is possible to detect the ion beam having large aberration of energy with high accuracy. It is also possible to increase the degree of focusing of the deflected beam by applying a voltage lower than that of the inside deflecting electrode 7 (if the ion is positive); (if the ion is negative, a voltage higher than that of the inside deflecting electrode 7 is applied).

A third embodiment will be explained next with reference to Figs.9A and 9B. While in the first embodiment both the outside deflecting electrode 6 and the inside deflecting electrode 7 are formed by using a plane electrode, in the third embodiment, either one of them or both of them are formed by using a curved electrode. As shown in Fig. 9A, while the inside deflecting electrode 7 is a plane electrode arranged in parallel with the direction of injection of the ion beam, the outside deflecting electrode 6 is a curved electrode so arranged that the distance between the outside deflecting electrode 6 and the inside deflecting electrode 7 becomes short as the coordinate of the direction (z direction) of injection of the ion beam increases. Because the rate of increase of the electric field in a direction of the deflection (y direction) as compared with the z coordinate is larger than that of the first embodiment, this configuration is effective when it is desirable to deflect extremely the ion with higher energy.

It should be appreciated that both the inside deflecting electrode 7 and the outside deflecting electrode 6 can be formed by using the curved electrode. The distance between the outside deflecting electrode 6 and the inside deflecting electrode 7 becomes short as the coordinate of the direction (z direction) of injection of the ion beam increases. While in the first embodiment, the component of the electric field in the -z direction is generated at the region where the value of the z coordinate is large, in the third embodiment, the component of the electric field in the -z direction (opposite to the direction of injection) is generated in the entire region of the z coordinate. Further, the component of the electric field of the -z direction (a direction opposite to the direction of injection) increases as the value of the z coordinate increases. Accordingly, this embodiment is effective to increase the angle of deflection of the entire ion beam which includes from the ions with lower energy to the ions with higher energy.

A fourth embodiment will be explained next with reference to Figs. 10A and 10B. While in the third embodiment either one of the inside deflecting electrode 7 and the outside deflecting electrode 6 or both of them are formed by using a curved electrode, in the fourth embodiment, either the outside deflecting electrode 6 or the inside deflecting electrode 7 is formed by combining a plurality of plane electrodes in order to increase the rate of increase of the electric field in a direction (y direction) of the deflection as compared with the z coordinate as in the third embodiment.

While the inside deflecting electrode 7 of Fig.10A is a plane electrode arranged in parallel with the direction of the injection of the ion beam as in the first embodiment, the outside deflecting electrode 6 is formed with two plane electrodes connected to each other with the angles of the plane electrodes being changed with respect to the direction of the injection of the ion beam. The two plane electrodes are connected such that the electrode connected in the down stream direction of the ion beam injected into the deflecting portion A has a larger angle of arrangement of the electrode with respect to the direction of the injection of the ion beam than that of the other electrode of the two plane electrodes which form the outside deflecting electrode 6. Because the rate of increase of the electric field in a direction (y direction) of the deflection as compared with the z coordinate is larger, this configuration is effective when it is desirable to deflect extremely the ions with higher energy. Further, because a plurality of plane electrodes are connected with the angles of the electrodes being changed to each other, it is easy to fabricate.

It should be appreciated that a plurality of plane electrodes 6A, 6B and 6C can be arranged in parallel with the direction of the ion beam injected into the deflecting portion A, with the distance between each of the plane electrodes and the inside deflecting electrode 7 being shortened gradually according to the increase of the value of the z coordinate. Because the curved electrode is not used in the fourth embodiment, it is easy to fabricate the electrode as compared with the third embodiment. Further, it is possible to obtain the same effects as in the third embodiment.

A fifth embodiment will be explained next with reference to Fig.11. In embodiments 1 to 4, by utilizing the fact that ions are separated or dispersed spatially according to respective energy when the ions are deflected at the deflecting portion A, the stronger electric field in the focusing direction is generated in a space where ions with higher energy are distributed, and the weaker electric field in the focusing direction is generated in a space where ions with lower energy are distributed. Further, by generating an extracting electric field in the vicinity of an injection port for the ion detector, the ion beam becomes focused.

In the present embodiment, electrodes 26 and 27 are arranged in the focusing portion B so that the distribution of the electric field can be substantially symmetric like a mirror operation with respect to a plane perpendicular to the collimated ion beam deflected by the deflecting field generated in the deflecting portion A. Hereinafter, these electrodes 26 and 27 are referred to as an outside focusing electrode and an inside focusing electrode, respectively. Electrode 27 is also a mesh electrode like electrode 7. It is not necessary to make the electrodes 26 and 27 of a mesh. However, if the mesh electrode is used for the electrode 26, it is possible to prevent the contamination of the electrode and prevent the neutral gas from staying in the deflecting and focusing part 5 and flowing in a direction of the ion detector.

In the arrangement of the electrodes of the focusing portion B according to the present embodiment, the distribution of the electric field at the focusing portion B has the following characteristics. The component in the -z direction of the electric field increases as the value of the y coordinate increases, and the component in the z direction of the electric field decreases as it decreases (see Fig.13B).
The ion with lower energy is deflected by the electric field of the deflecting portion A at a portion where the value of the z coordinate is small, and receives the force in the direction along the symmetric plane between the electrodes 7 and 27. And then, it is injected into the electric field generated at a portion where the value of the y coordinate is small in the focusing portion B, and receives the force of the -z direction.

Because the velocity of the ion with higher energy is fast in the z direction, it is deflected at a portion in the deflection portion A where the value of the z coordinate is large. Then, it hardly receives the force, because it passes around the connection portion of the electrodes 7 and 27. However, it is soon injected into the electric field of the focusing portion B at a portion where the value of the y coordinate is large, and receives large force of the -z direction.

Accordingly, the larger the energy of the ion is, the larger the focusing force of the -z direction exerts on the ion, and the smaller the energy of the ion is, the smaller the focusing force of the -z direction exerts on the ion. Because the distribution of electric field is substantially symmetric like a mirror operation with respect to a surface perpendicular to the ion beam deflected in parallel by the deflecting field generated in the deflecting portion A, the ion beam which passes through the electric field also traces the trajectory symmetric like a mirror operation. Accordingly, the ion beam can be focused finely.

A sixth embodiment will be explained next with reference to Figs.12, 13A, 13B, 14A and 14B. In this embodiment, a multiplier is used as an ion detector, the electrodes are arranged so as to be substantially symmetric like a mirror operation, and the same voltage (-1.3 kV) as a first electrode of the multiplier for generating secondary electrons is applied to the inside deflecting electrode 7, the inside focusing electrode 27 and the housing of the multiplier. In Fig. 13A, the outside deflecting electrode 6, the outside focusing electrode 26 and the electrode 17 are at the ground level (0 V). Fig.13B shows a result of calculation of the distribution of the electric field for the entire electrode system. Fig.13A illustrates a result of an analysis of an ion trajectory calculated with the result of analysis of Fig.13B, in which the ion beam having the aberration of energy of 5 to 2000 eV is injected into the deflecting and focusing part 5.

It is seen from Fig.13A that the ion beam having large aberration of energy can be focused finely after the deflection. Because the same voltage as the first electrode of the multiplier is applied to the inside deflecting electrode 7, the inside focusing electrode 27 and the housing of the multiplier, it is not necessary to provide an additional power source.

It is not necessary to form the electrodes used in the deflecting and focusing part 5 so as to allow the deflecting portion A to be strictly symmetric with the focusing portion B like a mirror operation. Fig.14A shows such an example that the deflecting portion A and the focusing portion B are not strictly symmetric with each other like a mirror operation. In Fig. 14A, the length of the y direction of the focusing portion B is shorter than that in the example symmetric like a mirror operation as in Fig. 13A. In addition, the electrode 17 parallel with the z direction and in the vicinity of the multiplier is provided at a position where the value of the y coordinate is larger than the electrode in the example symmetric like a mirror operation. Accordingly, in the example of Fig. 14A, the degree of the symmetry is less than that in the example of Fig. 13 (particularly between the electrodes 7 and 27). Fig. 14B shows a result of calculation of the distribution of the potentials when the same voltage as the example of Fig. 13 is applied to that of Fig. 14A. Further, Fig. 14A shows a result of analysis of the ion trajectory calculated with the result of analysis of Fig.14B, in which the ion beam having the aberration of energy of 5 to 2000 eV is injected into the deflecting and focusing part 5.

It is seen from these figures that even if the electrodes are out of the symmetric position, it is possible to focus the ion beam sufficiently. Basically, even if the arrangement of the electrodes is not completely symmetric like a mirror operation, it is possible to attain the desired object, by providing the injection port of the ion detector or the multiplier at a position where the ion with higher energy experiences stronger deflecting and focusing force, the ion with lower energy experiences weaker deflecting and focusing force, and thus the width of the ion beam can be narrowed to the maximum. While in this embodiment the arrangement of the electrodes is substantially symmetric like a mirror operation, it is also possible to use the arrangement of the electrodes as described in embodiments 1 to 4 as the electrodes for the deflecting and focusing part 5. It is desirable to select the type of the electrode in accordance with the space where the deflecting and focusing part 5 and the ion detector or the multiplier are provided.

A seventh embodiment will be explained next with reference to Figs. 15, 16A, 16B, 17A and 17B. Where the housing of the multiplier is set to the ground level in the sixth embodiment of Fig. 12, as shown in Fig. 15, the multiplier is caused to be provided with an aperture 18 having substantially the same size as that of a mesh electrode 20 provided at the entrance portion of the first electrode 14, the aperture 18 being positioned at that portion of the housing of the multiplier onto which the mesh electrode 20 is projected, whereby the ions are made incident on the first electrode 14 through the aperture 18 and then the mesh electrode 20. Because the extracting electric field is generated in the opening portion, ions never bounce back even if the housing of the multiplier is set to the ground level. It is, therefore, possible to detect the ions. If the electrodes substantially symmetric like a mirror operation as shown in Fig. 5 are used as the electrodes for the deflecting and focusing part 5, the same voltage as the first electrode 14 of the multiplier is applied to the inside deflecting electrode 7 and the inside focusing electrode 27, as in the sixth embodiment.

Fig. 16B shows a result of calculation of the distribution of the potentials in the whole electrode system. Further, Fig. 16A shows a result of an analysis of the ion trajectory calculated with the result of analysis of Fig. 16B, in which the ion beam having the aberration of energy of 5 to 2000 eV is injected into the deflecting and focusing part 5.

As is seen from Fig. 16A, because the extracting electric field is generated at the opening portion, the ion beam focused sufficiently after the ion beam with large aberration of energy was deflected, travels to a mesh electrode 20 mounted on the entrance portion of the first electrode 14 without bouncing back. In Fig. 16, only the trajectories to the mesh electrode 20 were calculated, on the assumption that all of the ions which arrived at the mesh electrode 20 pass through the mesh electrode and are detected. Because the same voltage as the first electrode of the multiplier is applied to the inside deflecting electrode 7, the inside focusing electrode 27, it is not necessary to provide an additional power source.

While it has been heretofore studied in the example (hereinafter referred to as the vertical arrangement) in which the ion detector 8 is provided in a direction perpendicular to the direction of the ion beam injected into the deflecting and focusing part 5, an arrangement is possible such that the ion detector or the multiplier may be slanted in the direction of the ion beam injected into the deflecting and focusing part 5.

Fig. 17B shows a result of the distribution of the potentials calculated when the same voltage as the example of Fig. 16 is applied to each of the electrodes. Further, Fig. 17A shows a result of an analysis of the ion trajectories calculated with the result of analysis of Fig. 16B, in which the ion beam having the aberration of energy of 5 to 2000 eV and a mass-to-charge ratio (m/z) of 100 is injected into the deflecting and focusing part 5. Because in this embodiment the opening portion is directed into a traveling direction of the deflected beam, the ion beam can be focused sufficiently by the extracting electric field generated around the opening portion. It is, therefore, possible to detect the deflected beam with high efficiency.

Further, the deflected beam can be focused sufficiently by the extracting electric field generated around the opening portion, even if there is not provided the electrode 17 in Fig. 17. The result of the calculation proves that the ion beam can be injected into the first electrode with high efficiency. While two examples have been explained, namely, the case where the electrodes for the deflecting and focusing part 5 are substantially symmetric with each other like a mirror operation and the case where the ion detector is slanted as shown in Fig.17, it is possible to use the arrangement of the electrodes as described in embodiments 1 to 4. It is possible to select the type of the electrodes in accordance with the space where the deflecting and focusing part 5 and the ion detector 8 or the multiplier are provided.

An eighth embodiment will be explained next with reference to Figs. 18. In the embodiment 8, an ion trap type mass analyzer 21 is used as the mass analyzing part 4 shown in embodiments 1 to 7. The ion trap type mass analyzer 21 comprises a ring electrode 28, and two endcap electrodes 29, 30 positioned so as to face each other and sandwich the ring electrode 28.

The neutral sample to be mass-analyzed is injected into the space between the electrodes of the ion trap type mass analyzer 21, after the pre-processing part 1 and the moving bed eliminating part 2 in the pre-processing part 1. Then, the neutral sample collides with the electrons injected into the space between the electrodes through a central injection port 31 of the end cap electrode 29 from an electron gun 29 for producing ion, and thus the neutral sample is ionized.

Whether the ion trajectory is stable or unstable is determined by the coordinate position of the point (a,q) corresponding to the ion, namely, whether the point (a,q) is in a stability region or in an instability region shown in Fig. 19. Where, the trajectory of the ion with the mass-to-charge ratio (m/z) is in the quadruple electric field generated in the space between the electrodes by using a high frequency voltage Vcos Ω t and a direct-current voltage U which are supplied to between the end cap electrodes 29, 30 and the ring electrode 28 from a main power source for operation 23, $$a = 8eZU / (mr_0^2 \Omega^2), \quad q = 4eZV / (mr_0^2 \Omega^2) \quad (1)$$

where, e designates the quantum of electricity, Z an ionic charge number, the mass-to-charge ratio (m/z) or the mass number, and $r_0$ the inner diameter of the ring electrode.

The magnitude of the voltage supplied from the main power source 23 to the electrodes based on the range of mass-to-charge ratio (i. e., mass range) of the ion to be mass-analyzed is determined in the control system 25 by using the size of the ion trap electrode, the frequency f (= 2π Ω) of the applied high frequency voltage, etc.

In the present embodiment, as the voltage for operation, the direct current voltage is not applied, but only the high frequency voltage is applied to the ring electrode 28. In Fig. 19, all the ions are stably caught, corresponding to the points within the range of $0 \leq q \leq 0.908$, these being on the straight line of $a=0$ within the stability region.

As clearly seen from the above equation (1), the q value of the ion and the dominant vibration frequency in the quadruple electric field also are different when the mass number of the ion (the mass-to-charge ratio (m/z)) is different. Of the ions stably caught in the ion trap, only the ions with the desired mass-to-charge ratio (m/z) are picked up and separated according to their m/z. This is the principle of the ion trap type mass spectrometer.

Mainly, there are the following two methods of picking up only the ion with the desired mass-to-charge ratio (m/z).

1) The amplitude V of the high frequency voltage applied to the ring electrode is sequentially changed on the basis of the above equation (1). Then, the trajectories of the ions with different mass-to-charge ratio (m/z) are sequentially made unstable by bringing the point corresponding to each of the ions out of its stability region ($0 \leq q \leq 0.908$ and on the straight line of $a=0$). As a result, the ion is ejected from the space between the electrodes (a normal ejection method).

2) A supplementary AC electric field is generated, which has substantially the same frequency as the dominant frequency of the ion with the desired mass-to-charge ratio (m/z). The amplitude of vibration of the ion with the desired ratio of charge to mass is amplified and the ion is ejected from the space between the electrodes (a resonant ejection method).

There are known some resonant ejection methods of generating a supplementary AC electric field having substantially the same frequency as the motion frequency of the ion with the desired mass-to-charge ratio (m/z). The most normal method is as follows. Applied to the end cap electrodes 29 and 30 are the supplementary AC voltages with a specific frequency which are different in phase from each other by 180 degrees. A supplementary electric field which oscillates with a specific period is generated in the space between the quadruple electrodes, in addition to the quadruple electric field. Only the ions with the desired mass-to-charge ratio (m/z) resonate with the supplementary AC electric field and are ejected from the space between the end cap electrodes and the ring electrode. The amplitude of the main high frequency voltage is scanned, that is, the value q of each of the ion species is scanned by using the above equation (1). Further, the dominant frequency of each of the ion species also is scanned to become closer to the frequency of the supplemental AC voltage. Accordingly, by applying the supplementary AC voltage having a specific frequency and scanning the amplitude of the main high frequency voltage, the mass-to-charge ratio (m/z) of the resonance-ejected ion is thus scanned. Fig.18 shows also a power source 24 for applying the supplementary AC voltage.

By the above method, the sequentially mass-analyzed ions exit out of the ion trap type mass analyzer 21 through an ejection port 32 or ion detecting port of the ion trap. The ion beam is ejected along the symmetrical axis of rotation of the ion trap type mass analyzer.

Figs. 20A, 20B and 20C each shows a result of calculation of the kinetic energy when the ion with 100

(amu) is ejected in resonance, in which the
supplementary electric field is generated by applying
the resonance voltages with the amplitudes 2V, 10V, 20V
to the end cap electrode as shown in Fig.17, the ion
having its ionic charge number 1 and its mass number 100
(amu) and corresponding to the point (a=0, q=0.897)
within the stability region. These figures are a
distribution diagram for the ejected energy obtained
from the calculation on 1550 ions distributed uniformly
in the space between the quadruple electrodes. From the
distribution diagram, it is understood that the
dispersion of large energy occurs when the ions are
ejected from the ion trap.

It has been found that the energy dispersion
becomes larger as the amplitude of the resonance voltage
becomes greater, that is, the energy dispersion at the
time of the resonance ejection of the ions depends upon
the amplitude of the resonance voltage. The variation in
velocity of the ions when they are resonance-ejected
hardly depends upon the mass-to-charge ratio (m/z). It
has been proved from the result of calculation that the
energy dispersion of the resonance-ejected ions is
substantially proportional to the mass-to-charge ratio
(m/z) thereof. Referring to Fig. 20B, assumed that the
singly charged ion within the mass range 50 to 650 (amu)
is mass-separated by applying the resonance voltage of
10V, the range of the energy dispersion of the ejected
ions is about 135.5 eV when the mass of the ion is 50
(amu) and about 1787.5 eV when it is 650 (amu).
Therefore, when the mass-separation is performed within
the mass range of 50 to 650 (amu), the total range of
the energy dispersion is very large, i.e., approximately
200 eV.

Also in case of the normal ejection, the range of the energy dispersion of the ions is about 30 eV when the mass of the ion singly charged is 100 (amu). It has been understood from the result of calculation that it also is proportional to the mass-to-charge ratio (m/z).

In a normal two-dimensional quadruple type mass spectrometer, the ions can be injected into the mass analyzing part with almost the same energy regardless of the mass of the ions. Therefore, the energy dispersion is small regardless of the mass of the ions. Further, in a sector type mass spectrometer, normally, double focusing (directional focusing and energy focusing) is performed. Therefore, the width of the energy dispersion is small as in the above case. As seen from the above description, the problem that the width of the energy dispersion becomes large is characteristic of the ion trap type mass spectrometer.

Accordingly, the deflecting and focusing part 5 used in the present invention is very useful when an ion trap type mass analyzer is used for the mass analyzing part 4. In the case, any type of electrode explained in the embodiments 1 to 6 can be used as the electrodes in the deflecting and focusing part 5. Similarly, any type of ion detector or multiplier can be used.

As understood from the result of calculations shown in Figs. 20A, 20B and 20C, the degree of the energy dispersion of the ejected ions depends upon the amplitude of the supplementary AC voltage (in case that the ions are resonance-ejected) and the mass-to-charge ratio (m/z) of the ions. Accordingly, it is possible to determine the magnitude of the voltage applied to the inside deflecting electrode 7 in the control system 10 of Fig.18 on the basis of the variation in energy corresponding to the mass-to-charge ratio (m/z) of the ions and the amplitude of the supplementary AC voltage (in case that the ions are resonance-ejected). It should be appreciated that in such a case, the voltage corresponding to the energy dispersion of each ion can be applied to the inside deflecting electrode 7 in accordance with the mass-to-charge ratio (m/z) to be mass-separated within the mass range and in cooperation with the control system 25 for the ion trap type mass analyzer for controlling the scanning of the ratio of charge to mass of the ions to be mass-analyzed.

The voltage to be applied to the inside deflecting electrode 7 may be determined according to the maximum value of the mass range of the ions to be mass-analyzed. For example, assumed that the mass range for a monovalent positive ion is within the range of 50 through 650 (amu). In this case, such a voltage that the ion having the energy of 1787.5 eV or slightly more, for example, 1800 eV to 2000 eV, is deflected and then effectively focused, is applied to the inside deflecting electrode 7, in consideration that the ejection energy of the ion with 650 (amu) is around 1787.5 eV.

Assumed that the scanning for mass-separating is performed within a predetermined range of the mass-to-charge ratio (m/z). The magnitude of the voltage to be applied to the inside deflecting electrode 7 can be determined so that the ions with a maximum value of the maximum mass-to-charge ratio (m/z) in a predetermined range thereof can be deflected, focused and detected with a high efficiency even though such ions have the maximum variation in energy when they are resonance-ejected. If such a voltage is applied to the inside deflecting electrode 7 all through the scanning of the mass-to-charge ratio (m/z) of the ions to be mass-separated, all the ions within the predetermined range of mass-to-charge ratio (m/z) can be deflected, focused and detected with a high sensitivity and with a high efficiency without expanding the ion beam. Accordingly, it is not required to adjust the deflecting voltage, etc.

According to the present invention, it is possible to avoid noises due to neutral molecules by detecting the mass-analyzed ions after deflecting them. Further, the expansion of an ion beam due to the energy aberration can be suppressed. Therefore, an improved mass spectrometer can be provided in which the ion can be detected with a high sensitivity and with a high efficiency.